United States Patent
Duncan et al.

(10) Patent No.: US 10,449,215 B2
(45) Date of Patent: Oct. 22, 2019

(54) NO CONTAINING COMPOSITIONS

(71) Applicant: University Court of the University of St. Andrews, St. Andrews, Fife (GB)

(72) Inventors: Morven Duncan, Fife (GB); Stewart Warrender, Fife (GB); Russell Edward Morris, Fife (GB); Damiano Cattaneo, Fife (GB)

(73) Assignee: University Court of the University of St. Andrews, St Andrews Fife (GB)

( * ) Notice: Subject to any disclaimer, the term of this patent is extended or adjusted under 35 U.S.C. 154(b) by 0 days.

(21) Appl. No.: 15/547,670

(22) PCT Filed: Jan. 28, 2016

(86) PCT No.: PCT/GB2016/050183
§ 371 (c)(1),
(2) Date: Jul. 31, 2017

(87) PCT Pub. No.: WO2016/124889
PCT Pub. Date: Aug. 11, 2016

(65) Prior Publication Data
US 2018/0264033 A1 Sep. 20, 2018

(30) Foreign Application Priority Data

Feb. 3, 2015 (GB) .................................. 1501779.1
Oct. 8, 2015 (GB) .................................. 1517841.1

(51) Int. Cl.
*A61K 33/00* (2006.01)
*A61K 31/155* (2006.01)
(Continued)

(52) U.S. Cl.
CPC ................ *A61K 33/00* (2013.01); *A61K 8/19* (2013.01); *A61K 9/143* (2013.01); *A61K 31/155* (2013.01);
(Continued)

(58) Field of Classification Search
CPC ........ A61K 33/00; A61K 47/52; A61K 9/143; A61K 31/496; A61K 8/19; A61K 31/155;
(Continued)

(56) References Cited

U.S. PATENT DOCUMENTS

| 4,954,526 A | 9/1990 | Keefer |
| 2002/0094985 A1 | 7/2002 | Herrmann |

(Continued)

FOREIGN PATENT DOCUMENTS

| CA | 967725 A | 5/1975 |
| CN | 104056598 | 9/2014 |

(Continued)

OTHER PUBLICATIONS

Liu et al., :Metformin enhances nitric oxide production and diminishes Rho kinase activity in rats with hyperlipidemia Biomed Central, 2014, pp. 1-7. (Year: 2014).*

(Continued)

*Primary Examiner* — Ernst V Arnold
*Assistant Examiner* — Kyung S Chang
(74) *Attorney, Agent, or Firm* — Beusse Wolter Sanks & Maire; Eugene J. Molinelli

(57) ABSTRACT

Disclosed are metal organic framework materials (MOFs), comprising an extra-framework NO releasing compound within the internal pores and/or channels of the MOF, the NO-releasing compounds and their preparation and uses. The MOFs and NO-releasing compounds are capable of releasing NO on application of an external stimulus and may provide materials with multiple modes of antibacterial and/or drug action.

12 Claims, 23 Drawing Sheets

(51) Int. Cl.

| | | |
|---|---|---|
| A61K 47/52 | (2017.01) |
| A61K 8/19 | (2006.01) |
| A61K 9/14 | (2006.01) |
| A61K 31/496 | (2006.01) |
| B01J 20/28 | (2006.01) |
| B01J 20/22 | (2006.01) |

(52) U.S. Cl.
CPC ............ *A61K 31/496* (2013.01); *A61K 47/52* (2017.08); *B01J 20/226* (2013.01); *B01J 20/28097* (2013.01); *A61K 2800/22* (2013.01); *A61K 2800/56* (2013.01)

(58) Field of Classification Search
CPC ............ A61K 2800/22; A61K 2800/56; B01J 20/28097; B01J 20/226
See application file for complete search history.

(56) References Cited

U.S. PATENT DOCUMENTS

| | | | |
|---|---|---|---|
| 2009/0233995 A1* | 9/2009 | Lautt .................... | A61K 31/155 514/440 |
| 2012/0070353 A1 | 3/2012 | Trukhan et al. | |

FOREIGN PATENT DOCUMENTS

| | | |
|---|---|---|
| CN | 104056599 | 9/2014 |
| WO | 94/08894 A1 | 4/1994 |
| WO | 1995/024908 | 9/1995 |
| WO | 2002/088148 | 11/2002 |
| WO | 2005/003032 | 1/2005 |
| WO | 2008/020218 | 2/2008 |
| WO | 2012/020214 | 2/2012 |
| WO | 2013/040415 A1 | 3/2013 |
| WO | 2013/186542 | 12/2013 |
| WO | 2014/012074 | 1/2014 |

OTHER PUBLICATIONS

Hrabie et al., "Chemistry of the nitric oxide-releasing diazeniumdiolate ("nitrohydroxyamine") functional group and its oxgen-substituted derivatives", Chem. Rev. 2002, 102, pp. 1135-1154. (Year: 2002).*
Southan et al., "N-nitrosated N-hydroxyguanidines are nitric oxide-releasing diazeniumdiolates", Chem. Commun., 1998, pp. 1191-1192. (Year: 1998).*
Jora,ptp et al., "Release of nitric oxide together with carboncentered radicals from N-nitrosamines by ultraviolet light irradiation", Free Radical Research, vol. 35, 2009, pp. 803-813. (Year: 2009).*
Ingelson, M., et al., Nitric Oxide Chemisorption in a Postsynthetically Modified Metal-Organic Framework, Inorg. Chem. 2009, pp. 9986-9988, vol. 48, No. 21, DOI: 10.1021/ic9015977, Publisher: American Chemical Society.
Lowe, A., et al., "Storage and delivery of nitric oxide via diazeniumdiolated metal organic framework," Microporous and Mesoporous Materials 2013, pp. 17-22, vol. 181.
IPO/EP: International Patent Application No. PCT/GB2016/050183, International Search Report and Written Opinion, dated May 2, 2015, pp. 1-19.
United Kingdom Search Report for correspondence GB Application 1501779.1 dated Dec. 1, 2015, pp. 1-5.
Allan, P., et al, , "Metal-organic frameworks for the storage and delivery of biologically active hydrogen sulfide", Dalton Transactions, 2012 , vol. 41, Issue 14, pp. 4060-4066.
Bao Z., et al, "Adsorption of Ethane, Ethylene, Propane, and Propylene on a Magnesium-Based Metal-Organic Framework", Langmuir, vol. 27, pp. 13554-13562 (2011).
Chen J, et al, "Synthesis, Structure and fluorescence of { [Na CU (BTC) (H20)4] 2H20}, a double-sheet coordination polymer with 2D network", Acta Chimica Sinica, vol. 62, Issue 23, pp. 2323-2328 (2004).

Dietzel P, et al, "Hydrogen adsorption in a nickel based coordination polymer with open metal sites in the cylindrical cavities of the desolvated framework", Chem. Comm., 2006, vol. 9, pp. 959-961.
Diring S, et al, "Localized cell stimulation by nitric oxide using a photoactive porous coordination polymer platform", Nature Communications, 2013, pp. 1-8.
Du H., et al, "A hierarchical supra-nanostructure of HKUST-1 featuring enhanced H2 adsorption enthalpy and higher mesoporosity", Cryst. Eng. Comm., 2011, vol. 13, pp. 1-3.
El Din, G, et al,., "NO-donors, part 9 [1]: diazeniumdiolates inhibit human platelet aggregation and induce a transient vasodilatation of porcine pulmonary arteries in accordance with the NO-releasing rates" Eur. J. Med. Chem., vol. 40, pp. 281-287 (2005).
Frank S, et al, "Nitric oxide drives skin repair: novel functions of an established mediator", Kidney international, vol. 61, 2002, pp. 882-888.
Ghermani N, et al., "Covalently bonded infinite zigzag chain structure in a novel Zn(II) complex of 2,5-dihydroxy-1,6-benzenedicarboxylic acid", Polyhedron, 2007, vol. 26, pp. 2880-2884.
Heilman B., et al, "Light-Triggered Eradication of Acinetobacter baumannii by Means of NO Delivery from a Porous Material with an Entrapped Metal Nitrosyl", J. Am. Chem. Soc., 2012, vol. 134, Issue 28, pp. 11573-11582.
Holmes K, et al., "Honeycombs, herringbones and brick-walls; three-fold guest-dependent variation in copper trimesate complexes bearing sulfimide ligands", Dalton Trans., 2004, pp. 3488-3494.
Ignarro LJ, "Biosynthesis and metabolism of endothelium-derived nitric-oxide", Ann. Rev. Pharmacol. Toxicol., vol. 30, pp. 535-560, 1990.
Imaz, et al, "Metal-biomolecule frameworks (MBioFs)", Chem. Commun., 2011, vol. 47, pp. 7287-7302.
Keefer K, et al., "Chemistry of the Diazeniumdiolates I. Structural and Spectral Characteristics of the [N(O)NO]-Functional Group", Nitric Oxide, 2001, vol. 5, Issue 4, pp. 377-394.
Li H, et al, "Design and synthesis of an exceptionally stable and highly porous metal-organic framework", Nature, vol. 402, pp. 276-279, 1999.
Lowe A., et al, "Storage and delivery of nitric oxide via diazeniumdiolated metal organic framework", Micropor. Mesopor. Mat., 2013, vol. 181, pp. 17-22.
Maragos C, et al., "Complexes of NO with nucleophiles as agents for the controlled biological release of nitric-oxide-vasorelaxant effects", J. Med. Chem, vol. 34, pp. 3242-3247, 1991.
McKinlay A., et al, "Exceptional Behavior over the Whole Adsorption-Storage-Delivery Cycle for NO in Porous Metal Organic Frameworks", J. Am. Chem. Soc., 2008, vol. 130, pp. 10440-10444.
Morris R, and Wheatley P., "Gas Storage in Nanoporous Materials", Angew. Chem. Int. Ed., 2008, vol. 47, Issue 27, pp. 4966-4981.
Nguyen J, et al, "Postsynthetic diazeniumdiolate formation and NO release from MOFs", Cryst Eng Comm, vol. 12, pp. 2335-2338 (2010).
Pal S., et al, "Metallopharmaceuticals based on silver(I) and silver(II) polydiguanide complexes: activity against burn wound pathogens", Antimicrob. Chemother., 2010, vol. 65, Issue 10, pp. 2134-2140.
Pal S., et al, "Synthesis of Highly Antibacterial Nanocrystalline Trivalent Silver Polydiguanide", J. Am. Chem. Soc., 2009, vol. 131 (44), 16147-16155.
Rojas S, et al., "Metal-organic frameworks as potential multicarriers of drugs", Cryst. Eng. Comm, 2013, vol. 15, pp. 9364-9367.
Rosi N., et al, "Rod Packings and Metal-Organic Frameworks Constructed from Rod-Shaped Secondary Building Units", J. Am. Chem. Soc, 2005, vol. 127, pp. 1504-1518.
Shabani M, et al., "Enhancement of wound repair with a topically applied nitric oxide-releasing polymer", Wound repair and regeneration, vol. 4, 1996, pp. 353-362.
Srinivasan A, et al., "Chemistry of the Diazeniumdiolates. 3. Photoreactivity" J. Am. Chem. Soc., 2001, vol. 123, pp. 5465-5472.
Tranchemontagne, DJ., et al, "Room temperature synthesis of metal-organic frameworks: MOF-5, MOF-74, MOF-177, MOF-199, and IRMOF-0", Tetrahedron, 2008, vol. 64, pp. 8553-8557.

(56) References Cited

OTHER PUBLICATIONS

Wheatley et al, "NO-Releasing Zeolites and Their Antithrombotic Properties" Journal of the American Chemical Society, vol. 128, pp. 502-509, 2006.

Works C, et al, "Photochemical Nitric Oxide Precursors: Synthesis, Photochemistry, and Ligand Substitution Kinetics of Ruthenium Salen Nitrosyl and Ruthenium Salophen Nitrosyl Complexes" Inorg. Chem., vol. 41, pp. 3728-3739, 2002.

* cited by examiner

NO CONTAINING COMPOSITIONS

CROSS-REFERENCE TO RELATED APPLICATIONS

This application is a 371 national stage application of PCT Application No. PCT/GB2016/050183, filed Jan. 28, 2016, and claims the benefit of United Kingdom Application No. 1517841.1, filed on Oct. 8, 2015 and United Kingdom Application No. 1501779.1, filed on Feb. 3, 2015; the entire contents of which are hereby incorporated by reference as if fully set forth herein.

FIELD OF THE INVENTION

The present invention relates to the formation of NO releasing compositions, particularly NONOate and N-nitroso compositions which enable the controlled release of NO and, optionally, other anti-microbial agents.

BACKGROUND TO THE INVENTION

The facility to control the release profile of anti-microbial or other active agents from compositions and materials is critical to their effectiveness to combat infection or contamination.

The initial rate and half-life of an active agent's release may be important factors in the efficacy of a material or composition. In addition, the facility to initiate or stimulate release of an active agent or a combination or agents by changing environmental factors can also play a vital role, e.g. by enabling targeted release of active agents.

Nitric oxide (NO) is a small molecule with anti-microbial properties and which has drawn considerable interest since it is also important in a range of biological processes. It is a vasodilator that increases blood flow through arteries and veins, and is also an important factor in controlling platelet adhesion and aggregation. It also plays a crucial role in the immune system. Much is now known about the mode of action of nitric oxide and it is clear that it has enormous potential in medicine and biotechnology in both in vivo and ex vivo applications.

The controlled delivery of nitric oxide may be important in therapy. For example, nitric oxide can prevent thrombosis and restenosis following balloon angioplasty and stent insertion in blocked arteries (International Patent Application WO 95/24908). The delivery of nitric oxide to the skin may also have therapeutic benefits for patients with peripheral circulatory problems which can occur in conditions such as arthritis and Raynaud's syndrome. Nitric oxide also plays a part in wound healing and angiogenesis, and delivery of nitric oxide to wounds can be beneficial when healing is slow which can occur, for example, in elderly patients (M. Shabani et al, Enhancement of wound repair with a topically applied nitric oxide-releasing polymer *Wound repair and regeneration*, 4, 353, 1996 and S. Frank H. Kampfer, C. Wetzler, J. Pfeilschifer, Nitric oxide drives skin repair: Novel functions of an established mediator *Kidney International*, 61, 882, 2002).

However, the delivery of nitric oxide to the desired area, and in the required optimum dose is often difficult because nitric oxide is a gas. Delivery of nitric oxide is difficult in both ex vivo e.g. biotechnology applications and in vivo e.g. medical applications.

Various methods of nitric oxide delivery are known such as
(a) molecules which release NO spontaneously;
(b) molecules which are metabolised to give NO;
(c) molecules that release NO on photoactivation;
(d) release of NO from polymers and polymer coatings;
(e) Release of NO from zeolites and metal organic frameworks (MOFs)

The class (a) of molecules include nitric oxide nucleophile complexes (NONOates) (C. M. Maragos et al., Complexes of NO with nucleophiles as agents for the controlled biological release of nitric-oxide-vasorelaxant effects *J. Med. Chem*, 34, 3242, 1991). A number of functional groups are capable of complexing with NO, however most commonly NONOates are formed from primary and secondary amines (e.g. as described in U.S. Pat. No. 4,954,526) in which NO binds to the amine moiety, and preferably a secondary amine. These NONOates may also be known as diazeniumdiolates.

At present, the use of NONOates in therapy is limited because they become distributed throughout the body which may compromise selectivity. An additional issue is that many NONOates are inherently unstable, with short shelf lives even at high pH, and comparatively short half-lives in biological conditions (of the order of minutes).

None the less, some NONOates have shown promise as controlled release substances, for releasing nitric oxide triggered by changes in temperature, pH, exposure to water or by photoactivation.

(Aloka Srinivasan, Naod Kebede, Joseph E. Saavedra, Alexander V. Nikolaitchik, Daniel A. Brady, Emily Yourd, Keith M. Davies, Larry K. Keefer and John P. Toscano *J. Am. Chem. Soc.* 2001, 13; 123(23):5465-72) describe photoactivated release of NO from NONOates. However, potentially toxic (e.g. carcinogenic) products resulting from alternative decomposition pathways remain a concern.

Lehmann et al. *Eur. J. Med. Chem.*, 19 Jan. 2005 reported the use of different diazeniumdiolates (NONOates) releasing NO. Among them a ciprofloxacin-diazeniumdiolate hybrid compound proven to release NO using a pH-temperature trigger. The NO liberation was reported only in aqueous buffer solution at pH 7.0-8.0, and the "burst effect" attributable to the trigger was relatively modest and of short half-life. Moreover, controlled release in this way from solution is unsuitable for many applications (e.g. wound dressing).

WO 2014/012074 describes NO-releasing coxib compounds (coxib compounds have use as anti-cancer agents) whereby different molecules containing a NO moiety deliver the gas through a metabolic pro-drug mechanism (i.e. class (b)).

The class (b) of molecules also include glyceryl trinitrate and sodium nitroprusside (L. J. Ignarro Biosynthesis and metabolism of endothelium-derived nitric-oxide *Ann. Rev. Pharmacol. Toxicol.* 30, 535, 1990). These compounds are currently widely used as vasodilators, however prolonged use can lead to toxic side products such as cyanides.

Furthermore, because the molecules in class (b) need to be metabolised to release NO, the targeting of NO to particular sites may also be poor resulting in the effects tending to be systemic.

In addition to certain diazeniumdiolates (NONOates), the class (c) includes metal complexes, such as the ruthenium complexes described by C. Works, C. J. Jocher, G. D. Bart, X. Bu, P. C. Ford, Photochemical Nitric Oxide Precursors *Inorg. Chem.*, 41, 3728, 2002. Overall, however, the range of chemistries from which photoinitiated NO release is possible remains limited. Moreover, the small molecules and complexes left over after NO release typically perform no other function and may even be associated with longer-term toxicity issues.

Class (d) release of nitric oxide mitigates the problems associated with systemic activity by delivering nitric oxide to a specific target site by supporting a nitric oxide releasing compound on a solid article. Such NO releasing compounds may be polymeric materials which can be coated onto medical instruments which can be used to target specific areas of the body for treatment. The polymers may contain, for example, the $N_2O_2$ group that releases NO after a chemical reaction (International Patent Application WO 95/24908 and US Patent Application 2002094985). However, the release of NO in such circumstances can be difficult to control and currently the preparation of the required materials may be expensive. The possible use of such polymers has been shown in the treatment of cardiovascular problems, for example, restenosis.

Class (e) also mitigates the problems associated with systemic activity by releasing the nitric oxide from a crystalline metal-exchanged porous aluminosilicate porous framework material called a zeolite (as described in the applicant's earlier international patent application WO 2005/003032). The reported capacity of these materials is acceptable at about 1 mmol of NO per g of zeolite and the materials have been shown to have anti-thromobosis properties (Wheatley et al. Journal of the American Chemical Society, 128, 502-509, 2006).

Storage and release of NO from metal organic framework materials (MOFs) has also been reported, for example in the applicant's earlier international patent applications, nos. WO 2008/020218, WO 2012/020214 and WO 2013/186542. The use of MOFs for the storage and controlled release of NO is also reported by R. E. Morris and P. S. Wheatley, *Angew. Chem. Int. Ed.*, 2008, 47, 4966, which reports exceptional performance in adsorption and release of NO over time from MOFs of CPO-27 structure, upon exposure to air and humidity.

Metal-organic frameworks (MOFs) are a class of nanoporous material. In these solids metal ions ($M^{n+}$) are linked together with organic units ($L^{y-}$) to form three dimensional networks. Many of these networks show good thermal stability and are extremely porous, with up to ~90% free volume. (O. M. Yaghi et al. *Nature*, 423, 705, 2003 (b) H. Li et al *Nature* 402, 276, 1999. (c) WO200288148-A).

A number of readily available and potentially useful MOF materials do not exhibit this behaviour towards storage and release of NO, however. In addition, although release triggered by contact with water, or only triggered by contact with water, is ideal for certain applications, this behaviour may be unsuitable for other applications. Additionally, the requirement for the NO loaded MOFs to be stored in dry inert conditions may also be limiting.

There are some reports of NO-releasing molecules being used as linkers in MOFs and related materials. A. Lowe, P. Chittajallua, Q. Gongb, J. Lib, K. J. Balkus Jr. *Micropor. Mesopor. Mat.* 2013, 181 (17-22) and J. L. Nguyen, K. K. Tananbe, and S. M. Cohen, *CrystEngComm* 2010, 12, 2335-2338 have reported a MOF structure made with a linker containing secondary amines. These amino groups can be used as bonding sites for nitric oxide (in contrast to the metal sites, for example as described by Morris et al., mentioned above). The resulting framework NONOate groups are able to release NO over time when exposed to high levels of humidity, elevated temperature and/or a pH change, but the overall NO capacity of the materials so far reported is limited.

There are also reports of NO storage in other classes of porous materials. For example, S. Diring, K. Kamei and S. Furukawa Nature Communications 2013, 2684 (4) describe boron imidazole frameworks capable of NO release upon exposure to UV light. However, since the nitric oxide is part of the linker, NO release degrades the linker and thus the framework. The NO release is therefore irreversible.

B. J. Heilman, S.t R. J. Oliver, and P. K. Mascharak *J. Am. Chem. Soc.*, 2012, 134 (28), pp 11573-11582 describes a manganese nitrosyl complex capable of photoactively releasing NO. The complex as a whole can be adsorbed into a porous material (e.g. AI-MCM-41), but this blocks the pores and prevents adsorption of any other molecules.

Accordingly, there remains a need for improved materials and compositions for the controlled release of antimicrobial agents, to address or mitigate one or more of the foregoing disadvantages.

SUMMARY OF THE INVENTION

An aspect of the invention is the provision of a bioactive molecule complexed to NO via a nitrogen-containing functional group forming a NONOate or N-nitroso compound, wherein the N-nitroso compound is formed by the complexation of NO to either an amine or imine moiety, or both.

According to a further aspect of the invention, there is provided a porous framework material, such as a metal organic framework material (MOF), comprising an extra-framework NO complexed compound, selected from a NONOate and/or N-nitroso compound within the internal pores and/or channels of the porous material or MOF. In some embodiments the porous framework material excludes a MOF.

NONOate compounds are formed from organic precursor compound having an electron-donating moiety capable of complexing to a nitric oxide molecule. The so-formed reaction intermediate may then complex to a further nitric oxide molecule. Thus, a NONOate is capable or releasing one, or more commonly two, equivalents of NO corresponding to each electron-donating moiety of the precursor (typically resulting in the formation, or re-formation of the precursor compound itself).

N-nitroso complexes comprise a single NO moiety bound to a nitrogen atom. Typically the N atom to which NO binds would belong to an amine group, however, the inventors have discovered that NO can also bind to imine moieties. A particular aspect of the invention is the unexpected discovery that in compounds containing both amine and imine moieties, such as guanidines and bi-guanidines, NO can bind preferentially to the imine N to form novel moieties such as

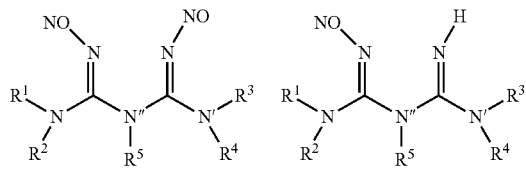

NONOate and/or N-nitroso compounds are capable of releasing NO and the inventors have found that the behaviour of such compounds in this regard is substantially unaffected by adsorption within a porous material/MOF framework. For example, the controlled release of NO from NONOates, and/or N-nitroso compounds (e.g. in response to a stimulus such as light, a change of temperature, pH etc.)

may still be effected from the extra-framework NONOate, and/or N-nitroso compound within the internal pores and/or channels of the material/MOF. Moreover, by virtue of their high internal surface area, high NONOate, and/or N-nitroso compound loading of MOFs is possible. The structure and properties of the MOF is also substantially unaffected by the NONOate, and/or N-nitroso compound guest species. Thus, the invention provides for the NO storage and release capabilities of NONOates, and/or N-nitroso compounds to be provided in combination with the known capabilities and uses of MOF materials.

Metal organic frameworks (MOFs) are a class of crystalline porous materials, in which metal ions ($M^{n+}$) or clusters of metal ions are linked together with linkers ($L^{y-}$) to form three dimensional networks, defining extended pores and channels of molecular dimension. The channel networks may extend in one, two or three dimensions. The channel networks may intersect and may define internal cavities. Metal organic frameworks may therefore be regarded as materials which define a large internal (and external) surface area. MOFs may be regarded as a class of zeotype materials.

It should be noted although the description is principally directed to the use of MOFs, this should not be construed as limiting and that other extended porous materials are also known, such as 2D and 1D coordination polymers, zeolites and zeotypes, mesoporous materials and organic framework solids. Such materials are to be considered as within the scope of the present invention and reference to MOFs hereinafter should not be construed as limiting.

The MOF may comprise a single type of metal ion, or more than one type of metal ion. The MOF may comprise metal ions of one or more transition metals, alkali metals, alkaline earth metals and/or other suitable metal cations, such as for example aluminium. The MOF may comprise ions of a metallic element in more than one oxidation state.

The MOF may comprise one or more framework transition metal ions selected from (but not limited to): $Ti^{n+}$, $V^{n+}$, $Cr^{n+}$, $Mn^{n+}$, $Fe^{n+}$, $Co^{n+}$, $Ni^{n+}$, $Cu^{n+}$, $Zn^{n+}$, $Ag^{n+}$, Ru, Rh where n is 1, 2, 3 or 4, depending on the metal and the oxidation state of that metal.

The MOF may comprise one or more framework transition metal ions selected from: $Cu^+$, $Cu^{2+}$, $Mn^{2+}$, $Mn^{3+}$, $Zn^{2+}$, $Fe^{2+}$, $Fe^{3+}$, $V^{3+}$, $V^{4+}$, $Ag^+$, $Ru^{3+}$, $Rh^{3+}$, $Ni^{2+}$, $Cr^{2+}$, $Co^{2+}$ and $Co^{3+}$. For example, the framework metal ion(s) may be selected from $Cu^+$, $Cu^{2+}$, $Cr^{2+}$, $Zn^{2+}$, $Co^{2+}$, $Co^{3+}$, $Ag^+$, $Ni^{2+}$, $Mn^{2+}$ and $Mn^{3+}$. Preferably the framework metal ion(s) are selected from $Cu^{2+}$, $Zn^{2+}$, $Ag^+$, $Ni^{2+}$, $Mn^{2+}$.

The MOF may comprise one or more framework alkali metal ions selected from, for example: $Na^+$ and $K^+$.

The MOF may comprise one or more framework alkaline earth metal ions selected from (but not limited to) $Ca^{2+}$ and $Mg^{2+}$, especially $Mg^{2+}$.

Other framework metal ions which may be present (alternatively or in addition to the above) may include for example $Al^{3+}$.

In some embodiments (e.g. for biological, medical and/or cosmetic applications), it may be preferred for the metal ions present in the MOF to be those which are deemed toxicologically acceptable for such uses, e.g. those metals which are considered to have acceptable/limited toxicity. Such considerations will depend on the circumstances of the use and may be determined by the skilled practitioner as appropriate. For example, the ions of Mg, Ca, Fe or Mn may be considered to have low toxicity. A balance may exist between acceptable toxicity and antimicrobial efficacy. For example Ag is known to demonstrate antimicrobial properties and has acceptable toxicity, as to the ions of Ni, Cu and Zn (which is less toxic but generally less antimicrobially active).

The MOF may comprise a single type of ligand, or more than one type of ligand. MOFs comprising more than one type of ligand and/or metal may be referred to as "mixed component" MOFs, or more specifically mixed-ligand or mixed-metal MOFs.

Each ligand may include one coordinating functional group, or more than one coordinating functional group. A coordinating functional group may comprise one atom or more than one atom which coordinates to a given metal ion.

For example, each ligand may include 2-10 coordinating sites, e.g. 2-6 coordinating sites, or 2-4 coordinating sites; for example 2 or 3 coordinating sites.

The MOF may comprise a polydentate ligand, for example a bidentate, tridentate or a ligand having another order of denticity.

The MOF may comprise carboxylate or polycarboxylate ligands, for example, benzene polycarboxylate ligands. A polycarboxylate ligand may be a polydentate (for example di- or tridentate) linking ligand.

A benzene polycarboxylate ligand may comprise a benzene ring and at least two carboxylate groups and, optionally, one or more further substituents to the benzene ring.

The MOF may be any suitable MOF with pore size large enough (such as greater than 4 angstroms in the smallest dimension) to accommodate a bioactive, NO-binding molecule. The MOF may be any suitable MOF with pore size large enough to accommodate a bioactive guanidine-, bi- or poly-guanidine-based molecule.

The MOF may comprise for example 1,4-benzenedicarboxylate, 1,3,5-benzene tricarboxylate (BTC), dihydroxy benzene dicarboxylate, in particular 2,5-dihydroxyterphthalate (DHTP) and/or the like.

The MOF may be, for example, MOF-74 (CPO-27), HKUST-1, STAM-1, MIL101 and SIP-3.

The MOF may comprise a biologically active ligand. For example: The MOF may comprise a nicotinate or isonicotinate ligand (i.e. the conjugate base of nicotinic acid, or a related species having a pyridine ring and at least one pendant carboxylate group). The MOF may comprise a fumarate ligand (i.e. the conjugate base of fumaric acid) or another unsaturated dicarboxylate, for example a MOF as described by Imaz et al., *Chem. Commun.*, 2011, 467, 7287-7302. The MOF may comprise a succinate (i.e. the conjugate base of succinic acid) or another paraffinic dicarboxylate. When released from the MOF (for example as the MOF decomposes over time) the said ligand may be a biologically active agent and so provide for a still further mode of action of the MOF of the present invention.

The MOF may comprise amine ligands, for example, 1,4-bipyridine or the like.

The MOF may comprise ligands having more than one type of co-ordinating moiety, such as 5-sulfoisophthalate ligands or the like.

The MOF may comprise more than one type of ligand.

The MOF may comprise or contain additional entities to those described above, for example, further metal or other positively charged ions, or other anionic species.

Further anions may include halogens, e.g. $Cl^-$, $F^-$, $Br^-$ or $I^-$ or other anions, e.g. $OH^-$ or $SO_4^-$.

The metal organic frameworks may in particular include species/molecules, within guest sites, such as pores or channels, formed in the framework. Such species may be for example water, solvent or other molecules e.g. derived from the components used in the manufacture of the framework.

One or more of the water molecules may be present as hydrating water molecules and be bound to the network structure, for example to a framework metal ion or a framework ligand.

As will be understood by a skilled reader, one or more water molecules may be disassociated, for example so as to form a protanated "$H_3O^+$" species and a coordinating $OH^-$ ligand, together with a further water molecule.

The total amount of water may vary depending on the degree of hydration of the MOF, for example due to variations in ambient humidity, temperature, contact with biological fluids, etc.

Hydroxide ligands may form part of the framework structure, and may be coordinated to more than one metal ion within the framework structure.

The invention is not limited to a particular MOF morphology or structural type. The MOF may for example be of the structural type STAM-1, CPO-27 or HKUST-1, the synthesis and properties of which are generally described in WO 2008/020218, WO 2012/020214 and WO 2013/186542, to which the skilled addressee is directed. The MOF may be of the structural type SIP-3.

An extra-framework species, such as the NONOate, and/or N-nitroso compound or another guest species, may be described as having been absorbed into a MOF. Such a species may be regarded as having been adsorbed to an internal surface of a MOF, within the pores or channels thereof.

The NONOate, and/or N-nitroso compound may be adsorbed to the MOF, i.e. to internal and external surfaces thereof.

The NONOate, and/or N-nitroso compound may be physisorbed or chemisorbed to the MOF.

The NONOate, and/or N-nitroso compound may be non-covalently bound to a surface (e.g. within a MOF), for example by electrostatic and/or Van der Waals forces, including dispersion forces. The NONOate, and/or N-nitroso compound may chemically interact with a surface, including forming covalent bonds to surface atom(s), or coordinating to surface atom(s).

The NONOate, and/or N-nitroso compound may interact (including chemically or physically binding to) framework metal ions, framework ligands and/or other extra-framework species such as water, or extra-framework cations or anions.

The NONOate, and/or N-nitroso compound may be reversibly adsorbed.

The NONOate, and/or N-nitroso compound may defuse out of the MOF over the course of time. The NONOate, and/or N-nitroso compound may be capable of being displaced by another species such as water or another small molecule on exposure of the MOF thereto. Alternatively or in addition, the NONOate, and/or N-nitroso compound may be capable of being released from the MOF responsive to a stimulus, such as a change in temperature or pressure, or irradiation with light, or contact with another species which may displace the NONOate, and/or N-nitroso from the MOF. The rate of release of the NONOate, and/or N-nitroso compound from the MOF may be altered (e.g. accelerated) by a stimulus.

NO may be released from the MOF (or from the NONOate, and/or N-nitroso, once released from the MOF itself) spontaneously over the course of time. For example, the NONOate, and/or N-nitroso compound may decompose so as to release NO over the course of time.

The NONOate, and/or N-nitroso compound may be capable of releasing NO following interaction with another species such as water or another small molecule on exposure of the MOF thereto (or on exposure of the free NONOate, and/or N-nitroso compound thereto). The NONOate, and/or N-nitroso (free and/or in the MOF) compound may be capable of releasing NO responsive to a stimulus, such as a change in temperature or pressure, or irradiation with light, or contact with another species. The rate of release of NO by the NONOate, and/or N-nitroso compound (and/or from the MOF) may be altered (e.g. accelerated) by a stimulus.

The NONOate, and/or N-nitroso may be irreversibly adsorbed, so as to be retained within the MOF indefinitely. The NONOate, and/or N-nitroso compound may be irreversibly releasably adsorbed, so as to be retained indefinitely within the MOF in the absence of a particular external stimulus, but be releasable therefrom if the external stimulus is applied. Similarly, the extra-framework compound remaining following release of NO from the MOF may similarly be reversibly, irreversibly or irreversibly releasably adsorbed. Irreversible releasable adsorption of NO may refer in particular to NO retained indefinitely within the MOF in the absence of water, but which is released from the MOF when contacted with moisture/humidity.

The NONOate, and/or N-nitroso compound may be formed from a precursor compound having an electron donating moiety, wherein the electron-donating moiety is an amine or imine, or group comprised of a combination of both amine and imine functionality such as a guanidine or bi-/poly-guanidine. The electron donating moiety may alternatively comprise another heteroatom as the electron donor—such as oxygen, phosphorus or sulphur. For example, the NONOate may be a sulfo-NONOate, formed from a precursor comprising a sulphite moiety. Similarly the nitroso compound may take the form of an N-oxide sulphonamide or S-nitrosothiol, or P-nitroso compound.

It is preferred that NONOates, and/or N-nitroso compounds used in connection with the present invention be stable, or have very long half-lives (of the order of days, weeks or months), at ambient temperatures and pressures and in the absence of an external stimulus (such as contact with water, irradiation with light, a change of pH).

The NONOate may comprise one or more functional groups of the general structure X:

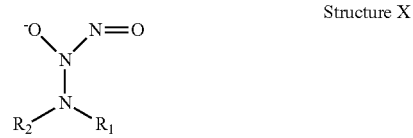

Structure X in which $R_1$ and $R_2$ may independently be carbon or heteroatom functionalities, such as an imine, amide, alkyl, aryl, allyl or the like, or H. $R_1$ and $R_2$ may together form an alicyclic or heterocyclic group;

the N-nitroso compound may comprise one or more functional groups of the general structures A-D:

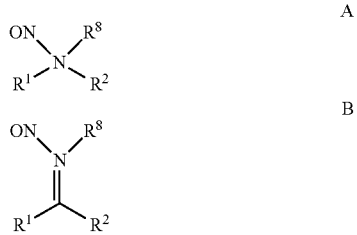

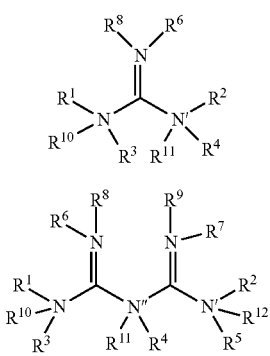

in which $R_1$-$R_{12}$ may independently comprise a substituted or unsubstituted C1-C10 alkyl-, aryl-, aldehyde-, carboxylic acid-, ester-, thiol-, phosphonate-, phosphinyl-, sulfonate-, boron- and/or amine-based moieties, H and/or halogen. Two or more R groups may together from part of a heterocyclic ring structure comprising one or more substituted or unsubstituted rings. Substituents being OH, halogen, $NH_3$, oxo, C1-C6 alkyl, phenyl and the like. At least one of $R_3$-$R_7$ may optionally be NO, in some circumstances only $R_6$ and/or $R_7$ in structure C and D may be NO. $R_8$-$R_{12}$ are each optional, but when present result in the N atom to which they are bound becoming positively charged. The functional group may be attached to or form part of a polymeric chain or macromolecule.

In some embodiments the structures are C and D above.

In an embodiment, $R_1$-$R_{12}$ may independently comprise substituted or unsubstituted $C_1$-$C_{10}$ alkyl-, aryl-, aldehyde-, carboxylic acid- and/or ester-based moieties, H and/or halogen. Substituents being OH, halogen, $C_1$-$C_6$ alkyl, or phenyl. At least one of $R_3$-$R_7$ may optionally be NO. $R_8$-$R_{12}$ are optional and when present introduce a positive charge to the nitrogen atom to which they are bound.

In another embodiment $R_1$-$R_5$ may independently comprise a substituted or unsubstituted $C_1$-$C_8$ alkyl- and/or phenyl-based (e.g. phenyl) moiety, or H. $R_6$ and/or $R_7$ are NO. Substituents being $C_1$-$C_6$ alkyl, phenyl, halogen. $R_8$-$R_{12}$ are absent.

The electron-donating moiety of the precursor compound may be a primary amine. Accordingly, one of $R_1$ and $R_2$ in structure A may be H, and $R_8$ is absent.

The electron-donating moiety of the precursor compound may be a secondary amine. The precursor compound may be a guanide, bi-guanide or bis-biguanide compound, for example.

The electron-donating moiety of the precursor compound may be a tertiary amine. The precursor compound may for example be a metronidazole or caffeine.

In a further aspect there is provided a biguanide compound comprising one or more NO molecules bound thereto, wherein the biguanide is obtainable by reacting a precursor compound having the general structure I:

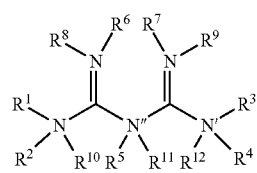

(I)

with NO gas or a nitrosylating agent in order to generate a bigaunide compound comprising one or more NO molecules bound thereto; wherein $R_1$-$R_5$ may independently comprise substituted and/or unsubstituted $C_1$-$C_{10}$ alkyl-, and/or aryl-based moieties (e.g. phenyl). $R_1$-$R_6$ may be H, with the proviso that $R_2$ is not H when $R_1$ is H, and $R_4$ is not H when $R_3$ is H.

$R_6$ and $R_7$ may independently be H, $C_1$-$C_{10}$ alkyl- and/or aryl-based moieties (e.g. phenyl), or together or independently may represent a coordinated metal ion, such as, but not limited to, silver, copper, nickel, zinc, magnesium and calcium.

$R_8$-$R_{12}$ are each optional, but when present result in the N atom to which they are bound becoming positively charged and may independently comprise H, $C_1$-$C_{10}$ alkyl- and/or aryl-based moieties (e.g. phenyl).

Substituents may comprise $C_1$-$C_{10}$ alkyl-, phenyl- and/or halogen moieties.

$R_1$-$R_7$ may be bound to an additional structure I (as defined herein and typically identical to the first structure) to form, for example, a bis or tris structure, such as a bis- or tris-biguanide.

The structure may be alone, or part of a polymeric chain or macromolecule in which the structure may also be repeated one or more times.

Conveniently $R_5$-$R_7$ and $R_8$-$R_{12}$, when present, may be H. Preferably $R_8$-$R_{12}$ are absent and $R_2$, $R_3$ and $R_{5-7}$ are H.

The above structure may be a N,N'-bi-substituted, N,N,N'-tri-substituted, N,N',N'-tri-substituted or N,N,N',N'-tetra-substituted molecule wherein each substituent is a non-H substituent.

A suitable nitrosylating agent may be $NOCl+CCl_4$),

In accordance with the above the precursor compound may form complexes with NO in different ways. Two (non-limiting) examples of possible forms are NONOate and N-nitroso complexes.

N-nitroso complexes comprise a single NO moiety bound to a nitrogen atom. Possible binding sites are shown below:

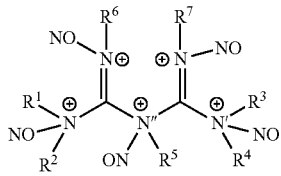

Where at least one of $R_1/R_2$ and $R_3/R_4$ are non-H substituents, as defined above in relation to structure I. The exact binding site will be dependent on the nature of the substituent R-groups. The above structure is depicted showing the nitrogens to which the NO group is attached as being quaternary. However it should be appreciated that said nitrogens may also be tertiary, such that an R group which is shown as being attached to a nitrogen is absent. For example the N-nitroso compound may be

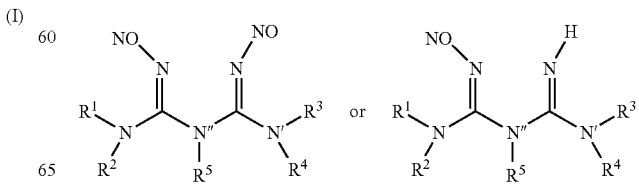

Possible NONOate binding sites are shown below:

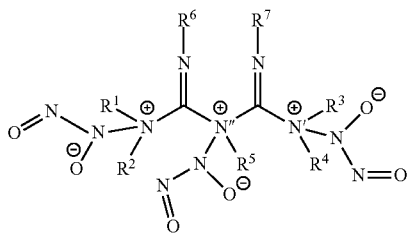

wherein $R_2$, $R_4$ and $R_5$ are H. One or more quaternary nitrogens may be tertiary as described above.

Exemplary compounds for use in accordance with the present invention include chlorhexidine, alexidine, proguanill, chlorproguanil, polyamino biguanide and polyhexamethyl biguanide.

The NONOate, and/or N-nitroso compound may be present as a salt (such that the MOF may comprise an extra-framework counter ion, e.g. of an alkali metal), or in a conjugate acid or base form.

The precursor compound may be a biologically active agent, such as an antibiotic, biocidal, fungicidal, sporicidal agent or the like. The precursor compound may be a drug compound, suitable for administering to a human or animal (topically, intravenously, orally etc). For example, the precursor compound may be a quinolone such as ciprofloxacin, or a biguanide such as chlorhexidine or a related compound, complex or salt thereof, or a sulfonomide, such as furosemide.

Advantageously therefore, NONOates, and/or N-nitroso compounds formed from an active precursor may release NO so as to re-form the active agent from which the NONOate, and/or N-nitroso compound was formed. Accordingly, the NONOate, and/or N-nitroso loaded MOF may have a first mode of action (release of the anti-microbial NO) and a second mode of action associated with release of the biologically active agent from which the NONOate, and/or N-nitroso compound was formed.

The precursor compound may itself have more than one mode of action. For example, the precursor compound may be in the form of a metal salt, wherein the metal ion itself has antimicrobial properties (e.g. silver salts, or nickel, zinc or copper salts, or mixed metal salts). Such salts may be loaded into the pores/channels of a MOF such that the MOF includes extra-framework NONOate, and/or N-nitroso species (typically anionic) and extra-framework metal ions, which may also be capable of being released from the MOF.

It is known that MOF materials themselves may comprise ligands and/or metal ions having biological activity. The invention may therefore provide for NONOate, and/or N-nitroso-loaded MOF materials having multiple modes of action, associated with the release of NO from the NONOate, and/or N-nitroso compound, release of the precursor compound from which the NONOate, and/or N-nitroso compound is formed, and in some embodiments release of a further biologically active agent and/or release of biologically active agents forming the MOF framework itself, during the eventual decomposition of the MOF material.

As will be described in further detail below, where a MOF in accordance with the invention has more than one mode of action, each mode of action may take place over a different timescale and/or be initiated or accelerated in response to a different stimulus.

Ciprofloxacin is a compound having the following structure:

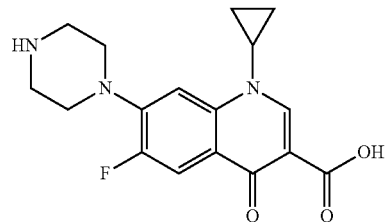 [SMILES: O=C(O)c1cn(C2CC2)c2cc(N3CCNCC3)c(F)cc2c1=O]

Chlorhexidine is a compound having the following structure:

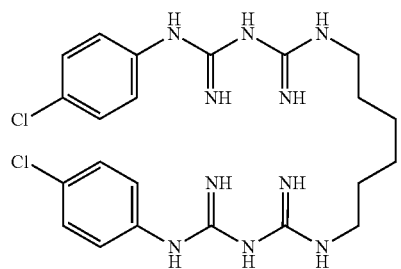 [SMILES: N=C(NCCCCCCNC(=N)NC(=N)Nc1ccc(Cl)cc1)NC(=N)Nc1ccc(Cl)cc1]

Furosemide is a compound having the following structure:

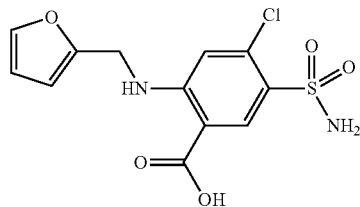 [SMILES: NS(=O)(=O)c1cc(C(=O)O)c(NCc2ccco2)cc1Cl]

Certain chlorhexidine salts may alternatively be regarded or referred to as chlorhexidine complexes, i.e. complexes of chlorhexidine and an acidic or basic compound or salt.

The inventors have found that chlorhexidine and related molecules and its salts (including but not limited to chlorhexidine diacetate, chlorhexidine dihydrochloride and chlorhexidine digluconate, and metal chlorhexidine salts, such as silver chlorhexidine) can be made to form stable NONOate, and/or N-nitroso compounds. A particular aspect of the invention is the unexpected discovery that in compounds containing both amine and imine moieties, such as guanidines and bi-guanidines, NO can bind preferentially to the imine N to form novel moieties such as

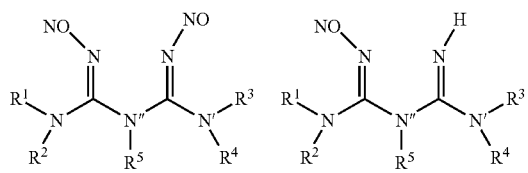

Related chlorhexidine molecules may take the form:

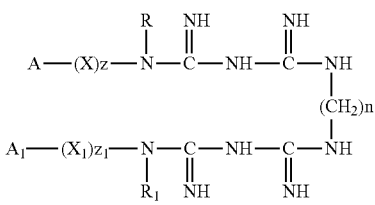

wherein A and $A_1$ each independently represent either a phenyl radical which optionally is substituted by an alkyl or alkoxy group containing from 1 to 4 carbon atoms, a nitro group, or a halogen atom; an alkyl group containing from 1 to 12 carbon atoms; or alicyclic groups containing from 4 to 12 carbon atoms; X and $X_1$ each independently represent an alkylene radical containing from 1 to 3 carbon atoms; z and $z_1$ each independently may be either 0 or 1; R and $R_1$ each independently represent hydrogen, an alkyl radical containing from 1 to 12 carbon atoms, or an aralkyl radical containing from 7 to 12 carbon atoms; and n is an integer from 2 to 12.

An exemplary compound is alexidine.

NONOate, and/or N-nitroso compounds may also be prepared from other biologically active precursors, such as ciprofloxacin or a ciprofloxacin salt or complex, furosemide or a furosemide salt or complex. In addition, the release profile of NO from the resulting NONOates, and/or N-nitroso may be altered in response to irradiation with light and/or moisture, allowing for controlled release of NO from these NONOates, and/or N-nitroso compounds. For example, release of NO from these materials may be triggered (e.g. by irradiation with light) so as to afford an initial burst followed by sustained release of NO (e.g. as the NONOate, and/or N-nitroso compound decomposes under ambient conditions). Accordingly, the invention may provide for a significant extension in the antimicrobial activity, in comparison to the precursor compounds/salts themselves.

Accordingly, in another aspect, the invention extends to a NONOate, and/or N-nitroso compound or salt, comprising a biologically active precursor having at least one secondary amine to which NO has complexed, to form NONOate, and/or N-nitroso moiety having the structure X or A, B, C, or D. The biologically active precursor species may be chlorhexidine, related molecule as defined, or a salt thereof, a chlorhexidine salt or complex, ciprofloxacin or a ciprofloxacin salt or complex, furosemide or a furosemide salt or complex.

Additionally, in another aspect of the invention there is provided a method of releasing NO, comprising providing a NONOate, and/or N-nitroso compound or salt, comprising a biologically active precursor species having at least one secondary amine to which NO has complexed, to form NONOate, and/or N-nitroso moiety having the structureX. A, B, C, or D; wherein the biologically active precursor species may for example be chlorhexidine, related molecule as defined or a salt thereof, a chlorhexidine salt or complex, ciprofloxacin or a ciprofloxacin salt or complex, furosemide or a furosemide salt or complex; and
irradiating the NONOate, and/or N-nitroso compound or salt with UV light so as to release NO therefrom and/or
exposing the NONOate, and/or N-nitroso compound or salt to moisture/humidity so as to release NO therefrom.

The inventors have also surprisingly found that NONOates, and/or N-nitroso compounds may be formed from these biologically active precursor compounds, using methods previously applied to load molecular sieve materials (such as zeolites and MOFs) with NO—for example as generally described by Morris and Wheatley (*Angew. Chem. Int. Ed.,* 2008, 47, 4966) or Lowe et al. (*Micropor. Mesopor. Mat.* 2013, 181 (17-22)), in which the molecular sieve is first activated and then loaded with NO.

The invention also extends in a further aspect to a method of preparing a NONOate and/or N-nitroso from a biologically active precursor having at least one secondary amine moiety (such as chlorhexidine, a related compound as defined or salt thereof, a chlorhexidine salt or complex, ciprofloxacin or a ciprofloxacin salt or complex, furosemide or a furosemide salt or complex), comprising;
activating the biologically active precursor by heating the precursor and/or exposing the precursor to a reduced pressure; and
exposing the activated precursor to NO.

Heating and/or exposing the precursor to a reduced pressure is thought to remove molecules which would otherwise bind to or stabilize the secondary amines, such that a higher proportion of secondary amines are available for subsequent complexing to the NO, so as to form the NONOate and/or N-nitroso compound.

The NONOate and/or N-nitroso compound may be from a biologically active precursor which has been adsorbed into the pores and/or channels of a MOF.

The method may comprise exposing the precursor to a high-vacuum (for example of the order of less than $10^{-2}$, $10^{-3}$ or $10^{-4}$ Torr).

The method may comprise exposing the activated precursor to one or more atmospheres of NO. The method may comprise exposing the activated precursor to around two, three or four atmospheres of NO.

The precursor may be activated for any suitable period of time, which may vary for example depending on the composition, purity or morphology of the precursor compound, or the activation conditions. Typically, for example, activation may take place over the course of around an hour.

Similarly, the activated precursor may be exposed to NO for a suitable length of time, for example one, two or more hours.

The skilled addressee will appreciate that the optimal conditions and duration of the steps may be determined by monitoring the progress of the reaction (for example by monitoring changes in pressure, gravimetric analysis, spectroscopically, and so forth).

A MOF in accordance with the invention may comprise a further biologically active agent, as a guest species within the pores and/or channels of the MOF. The further biologically active agent may be incorporated and stored in the pores/channels of the MOF and released into the environment either spontaneously (e.g. by diffusion) and/or in response to a stimulus (such as exposure to moisture or a chemical agent, increase in temperature etc.).

The further active agent may be released over a similar or a longer/shorter period than the release of NO from the NONOate and/or N-nitroso compound. The further active agent may act in a complimentary fashion to or synergistically with the NO.

The further active agent may be NO. The MOF may comprise irreversibly releasably adsorbed NO.

The MOF may conveniently be loaded with irreversibly releasably adsorbed NO at the same time as a NONOate and/or N-nitroso compound, or whilst forming a NONOate and/or N-nitroso compound from a precursor in situ.

A MOF loaded with an extra-framework NONOate and/or N-nitroso compound (which as mentioned above) may release NO spontaneously and/or in response to a stimulus.

Many further biologically active agents can be envisaged. The active agent may be a small molecules (such as carbon monoxide, hydrogen sulphide, a nitrogen oxide etc.), or an organic active agents (including, but not limited to, the following classes—penicillins (e.g. amoxicillin, penicillin), cephalosporins (all generations), aminoglycosides (e.g. neomycin, streptomycin), glycopeptides (vancomycin etc), macrolides (erythromycin etc). Anti-bacterial agents, anti-viral and/or anti-fungal agents could be stored and adsorbed in a similar fashion. The active agent could also be an extra-framework metal ion or metal nanocluster (e.g. silver, copper, zinc, nickel etc).

The active agent may be anti-microbial, and/or may serve to render a microbe contracted therewith more sensitive to NO. Alternatively, the further guest species may simply be a repelling molecule designed to repel microbes, such as may be used in anti-fouling applications.

The active agent may include a physiologically active drug molecule (by which we include both neutral or ionic species, such that extra-framework counter ions may also be present). A drug molecule may have no antibacterial activity in itself (e.g. an anti-cancer drug such as doxorubicin or another drug such as caffeine). A combination of NO and a drug molecule may help to combat a particular condition and prevent infection or bacterial contamination during treatment. Delivery of a combination of active agents has been proposed to retard the development of bacterial resistance.

The active agent may have anti-biofilm activity, i.e. it may cause bacterial biofilms to disassemble (particularly D-amino acids such as D-leucine, D-methionine, D-tyrosine, D-tryptophan etc, or mixtures of amino acids).

The MOF may comprise two or more further active agents.

According to another aspect of the invention, there is provided a method of preparing a MOF comprising an extra-framework NONOate and/or N-nitroso compound, in particular a MOF in accordance with other aspects;
the method comprising:
  forming a NONOate and/or N-nitroso from a suitable precursor compound; and contacting a MOF with the NONOate and/or N-nitroso compound so as to adsorb the NONOate and/or N-nitroso compound into the pores and/or channels of the MOF;
or the method comprising:
  forming a MOF comprising a precursor compound, capable of reacting to form a NONOate and/or N-nitroso compound, in the pores and/or channels of the MOF; and
  forming an extra-framework NONOate and/or N-nitroso compound in situ by contacting the MOF with NO.

The method may comprise contacting a MOF with a precursor compound capable of reacting to form a NONOate and/or N-nitroso, so as to adsorb the precursor compound into the pores and/or channels of the MOF.

The method may comprise forming a MOF around a precursor compound (or a NONOate and/or N-nitroso compound), for example by using the precursor compound (or NONOate and/or N-nitroso compound) as a template molecule for the MOF synthesis.

Accordingly, in an aspect of the invention, there is provided a metal organic framework material (MOF), comprising an extra-framework precursor compound capable of reacting to form a NONOate and/or N-nitroso compound, within the internal pores and/or channels of the MOF.

The method may comprise activating the MOF and/or the precursor compound.

The term "activated" refers to the MOF being presented in a state in which it is more receptive to adsorption of extra-framework or guest species than would otherwise be the case. Similarly, the term "activated" refers to the precursor compound being presented in a state in which it is more receptive to formation of a NONOate and/or N-nitroso complex. Activation may improve the rate of adsorption/reaction. Activation may increase the extent of adsorption/reaction.

Activation may involve the removal of unwanted molecules/species.

For example, activation of a MOF may involve the removal of guest molecules/species from the pores and/or channels of the framework (e.g. species present following synthesis of the MOF, or which have diffused into the MOF from the surroundings such as water), to allow other species to be more readily adsorbed into the MOF. Such guest molecules/species may obstruct diffusion through the pores/channels of the MOF, such that their removal may facilitate loading with another species (e.g. NO). Activation of the MOF may result in the MOF, for example framework metal ions, becoming less coordinatively saturated, thereby presenting a greater number and/or more reactive coordination or adsorption sites.

The available sites may be capable of strongly (irreversibly, or irreversibly releasably) binding to guest species which are subsequently introduced. The presence of irreversibly or irreversibly releasably adsorbed guest species may be indicated by a strong hysteresis between the adsorption and desorption arms of an adsorption/desorption isotherm. In contrast, a reversibly adsorbed guest species may be more weakly bound.

Similarly, activation of a precursor compound may involve the removal of molecules/species which might otherwise obstruct binding of NO, for example to an amine moiety of the precursor.

Activation of a MOF may also involve a change in structure of the framework to facilitate adsorption of guest species (e.g. the NONOate and/or N-nitroso compound). Moreover, activation of a precursor compound may involve a chemical change, such as a protanation or a deprotanation, which might render the precursor more susceptible to binding to NO.

The MOF may be activated prior to adsorption of the precursor compound or the NONOate and/or N-nitroso compound, as the case may be.

The precursor compound may be activated in situ; i.e. following adsorption into the pores/channels of the MOF.

A single activation step or process may result in the activation of both the MOF and a precursor compound adsorbed therein.

In some embodiments, the MOF may inherently allow a guest molecule (e.g. the NONOate and/or N-nitroso compound) to be adsorbed irreversibly, in which case activation may not be required, or activation may be used to increase the amount of guest molecule which may be adsorbed.

Activation may comprise heating the MOF and/or precursor compound. Typical temperatures which may be used for activation include a temperature up to about 450° C., for example, from about 20° C. to about 250° C., preferably, about 50° C. to about 150° C., most preferably about 80° C. to about 120° C., e.g. about 110° C. Lower temperatures may be appropriate for activation of a precursor compound, or of a MOF in which a precursor compound has been adsorbed.

Activation may comprise exposing the MOF and/or precursor compound to a reduced pressure (at ambient temperature or elevated temperature), for example generally as described above in relation to certain biologically active precursor compounds.

Typical pressures which may be used for activation include a pressure less than atmospheric pressure, e.g. less than 1 bar, such as from about $1 \times 10^{-4}$ mbar to about 1 bar.

Activation may comprise irradiation with light, e.g. ultraviolet light.

Activation, in particular of a MOF, may be achieved chemically. Chemical activation may be achieved using a chemical treatment method such as exposure of a MOF to a desired chemical or a mixture of chemicals. Examples of suitable chemicals include solvents such as acetonitrile ($CH_3CN$), dimethylformamide (DMF), ethanol (EtOH) or methanol (MeOH), supercritical carbon dioxide and the like.

Chemical activation may remove unwanted molecules, e.g. unwanted guest molecules from the MOF framework, by chemical displacement of the guest molecules by the molecules of the chosen activating chemical species.

Activation may comprise a combination of these steps. For example, activation may be achieved chemically, followed by one or more other non-chemical activation steps or vice versa.

A MOF may be partially activated, by removing only a portion of the guest species present, or by removing only certain types of guest species, or a MOF may be "fully" activated, by removing substantially all of the guest species from the framework.

The method may comprise contacting the MOF and/or the precursor (which may have been adsorbed into the MOF) to one or more atmospheres of NO. Contact with NO may be conducted at two, three or four atmospheres of NO.

Contacting a MOF and/or the precursor with NO at elevated pressure may facilitate formation of a NONOate and/or N-nitroso compound and/or adsorption of NO to the MOF framework itself.

Contacting a MOF and/or the precursor with NO at elevated pressure may give rise to a greater loading of NO.

Contacting a MOF and/or the precursor with NO at elevated pressure may provide for milder activation conditions. For example, to achieve a given NO loading (of a NO adsorbed into a MOF, as irreversibly releasably stored NO and/or as a NONOate and/or N-nitroso compound) a lower temperature of activation may be required, or activation may be achieved solely by reduced pressure.

Thus the invention further extends in an aspect to preparing a MOF comprising irreversibly releasably stored NO, the method comprising exposing the MOF to NO at an elevated pressure. The method may comprise activating the MOF before contacting it with NO at elevated pressure. The MOF may be activated by exposing the MOF to a reduced pressure.

The method may comprise contacting the MOF (including the MOF loaded with the precursor, or the NONOate and/or N-nitroso compound) with a further biologically active agent.

The MOF may be contacted with the further biologically active agent before, after, or concurrently with its contact with the NONOate and/or N-nitroso compound or the precursor compound, as the case may be.

The further biologically active agent may be NO, such that the method comprises preparing a MOF comprising adsorbed extra-framework NONOate and/or N-nitroso compound and adsorbed NO, which may be irreversibly releasably adsorbed NO.

Where the method comprises contacting a MOF loaded with the precursor compound (i.e. adsorbed into the pores and/or channels of the MOF), contacting the MOF with NO may cause the formation of an extra-framework NONOate and/or N-nitroso compound in situ, within the pores and channels of the MOF.

Contacting the MOF with NO may result in adsorption of NO into the pores and/or channels of the MOF. Adsorption of the NO into the MOF and in situ formation of the NONOate and/or N-nitroso compound may occur concurrently.

The adsorbed NO may be irreversibly releasably adsorbed.

The method may comprise activating the MOF prior to contact with NO.

The method may comprise using a single activation step. For example, the MOF loaded with the precursor compound may be activated (i.e. to at least partially activate both the precursor and the MOF itself) and then contacted with NO so as to form an extra-framework NONOate and/or N-nitroso compound in situ and irreversibly releasably adsorb NO.

Alternatively, the MOF may be activated and then loaded simultaneously with a NONOate and/or N-nitroso compound and NO (e.g. by contacting the activated MOF with a reaction mixture used to prepare a NONOate and/or N-nitroso compound), or indeed any other biologically active agent.

The method may comprise ion exchanging the MOF (prior to, after or as an intermediate step to those described above). Ion exchange may be achieved by any suitable method, for example by washing the MOF in an excess of a solution of a metal ion or ions. Ion exchange may comprise washing the MOF with a solution of a chelating agent, or some other agent or ligand capable of preferentially binding to extra-framework metal ions present, before subsequently washing with a solution of another metal ion.

The MOF may be prepared by any suitable method, as known in the art. For example, the MOF may conveniently be prepared by way of the low temperature aqueous synthesis as described in the applicant's co-pending application no. PCT/GB2013/051520.

In another aspect of the invention there is provided a method of releasing NO, comprising providing a MOF having an extra-framework NONOate and/or N-nitroso compound within the internal pores and/or channels of the MOF, contacting said MOF with a medium into which the NO is to be released, and releasing NO into the medium.

The method may comprise releasing NONOate and/or N-nitroso compound from the pores and/or channels of the MOF over a period of time, for example by diffusion under ambient conditions. The method may comprise releasing NO from the NONOate and/or N-nitroso compound over a period of time. NO may be released from the NONOate and/or N-nitroso compound whilst the NONOate and/or N-nitroso compound is within the MOF, and/or from NONOate and/or N-nitroso compound which has been release from the MOF.

The method may comprise applying an external stimulus to the MOF. The external stimulus may comprise an increase in temperature, a change in pH, irradiation with light, a change in pressure or a combination of these.

The external stimulus may comprise contacting the MOF with another species, such as water, so as to displace the NONOate and/or N-nitroso compound from the MOF and/or interact with the NONOate and/or N-nitroso compound to release NO.

The release of NO (and/or of the NONOate and/or N-nitroso compound from the MOF) may be initiated by the external stimulus. The rate of release of the NO may be altered (e.g. accelerated) by a stimulus.

Accordingly, the invention provides for release of NO (any further biologically active agent which may be present) in a controlled manner. The controlled release profile may be further tailored to particular requirements by the selection of the metal organic framework material itself, for example by virtue of the channel/pore dimensions, or adsorption properties of the framework ions or ligands.

The method may comprise irradiating at a particular frequency (e.g. with UV light). For example, certain NONOates and/or N-nitroso compounds may be sensitive to irradiation with UV light, which may cause the NONOate and/or N-nitroso compound to decompose so as to release NO. The inventors have found that this behaviour of NONOates and/or N-nitroso compounds is not adversely affected by their incorporation into MOFs.

The method may comprise releasing a further biologically active agent from the pores and/or channels of the MOF into the said medium.

As mentioned above, a NONOate and/or N-nitroso compound may be formed from a suitable precursor compound, which may itself be biologically active (for example a chlorhexidine compound, related compound or a ciprofloxacin compound). Moreover, the precursor compound may remain once the NONOate and/or N-nitroso compound has released NO. Accordingly, the further biologically active agent may be a said precursor compound.

The method may comprise releasing a metal ion from the pores and/or channels of the MOF. The metal ion may be present in the MOF as an extra-framework metal ion. The metal ion may be biologically active (e.g. $Ag^+$, which is antibacterially active).

The method may comprise releasing a component of the MOF, that is to say a framework metal ion and/or a framework ligand, into the said medium. The MOF may comprise framework metal ions and/or ligands which are biologically active agents.

The MOF may be capable of providing more than one "mode of action".

For example, the MOF may be capable of releasing more than one type of biologically active agent, each of which may exhibit a different biological activity (such as NO and chlorhexidine, for example). Indeed biologically active agents may act synergistically, such that their efficacy in combination exceeds the effect of either or both agents when applied individually.

The MOF may be capable of releasing biologically active agents over more than one timescale (which may be characterised by different half-lives). A first biologically active agent (e.g. NO) may be released over a first timescale (e.g. in a short initial burst) and a second biologically active agent (e.g. a precursor compound) may be released over a second timescale (typically a longer timescale).

Indeed, the MOF may be capable of releasing a given biologically active agent, in particular NO, over more than one timescale. For example, a NONOate and/or N-nitroso compound in the MOF may have a long half-life (of the order of hours or days) at ambient conditions and also be capable of releasing NO at a greater rate (shorter half-life) in response to an external stimulus such as exposure to UV radiation.

The MOF may be capable of releasing biologically active agents in response to more than one external stimulus. For example, the MOF may comprise irreversibly releasably adsorbed NO and extra-framework NONOate and/or N-nitroso compound. The method may comprise releasing irreversibly releasably adsorbed NO by contacting the MOF with moisture, and releasing NO from the NONOate and/or N-nitroso compound by irradiation with UV light.

Accordingly the method may comprise applying more than one external stimulus.

In addition, it has surprisingly been found that certain MOFs comprising adsorbed NO are also capable of releasing NO upon irradiation with UV light.

This behaviour has been observed for MOFs which comprise irreversibly releasably adsorbed NO, which have already been shown to be capable of releasing NO on contact with moisture (as described for example in references 3-6, below and in the applicants international applications nos. WO 2008/020,218, WO 2012/020,214 and WO 2013/186, 542; to which the skilled addressee is directed).

The method can be applied to MOFs that show humidity-triggered NO release, to afford additional control over the NO release initiation and profile from these materials.

The behaviour has also been observed for MOFs previously thought to substantially irreversibly adsorb NO, such as Mg-CPO-27 or HKUST-1 (a copper-based MOF). In such cases, the sample can be exposed to air (and the moisture therein) for long periods of time with low or no release of NO, and the NO release can be selectively achieved by irradiating with UV light.

Accordingly, in another aspect, the invention extends to a method of releasing NO, comprising providing a MOF having NO adsorbed, preferably irreversibly or irreversibly releasably, in the pores and/or channels of the MOF; and irradiating the MOF with UV light so as to release NO therefrom.

The MOF may be contacted with a medium into which the NO is to be released, and then irradiated, or vice versa. The medium into which the NO is to be released may comprise a species, such as water, which may itself stimulate release of NO.

The NO may be bound to framework metal ions.

The MOF may be any suitable MOF with pore size large enough to accommodate a bioactive, NO-binding molecule. The MOF may be any suitable MOF with pore size large enough to accommodate a bioactive guanidine-, bi- or poly-guanidine-based molecule as described herein The MOF may have the structural type CPO-27 or HKUST-1. The MOF may have the structural type MIL-101, STAM-1 or SIP-3.

The MOF may be based upon one or more framework metal ions selected from the list above. In particular, the MOF may comprise $Mg^{2+}$ (e.g. Mg-CPO-27), and/or $Zn^{2+}$ and/or $Ni^{2+}$ (e.g. Zn-CPO-27, Ni-CPO-27, MgNi-CPO-27, MgNiZn-CPO-27, NiZn-CPO-27), or $Cu^+$ (e.g. Cu-HKUST-1).

The method may comprise irradiating a MOF comprising one or more of the following types of framework ligand: di- or tri-carboxylate (e.g. a benzene carboxylate such as benzene 1,3,5-tricarboxylate, or a terephthalate such as 2,5-dihydroxyterephthalate or 1,4-terephthalate); an amine ligand (such as 1,4-bipyridine).

The MOF may comprise a ligand having more than one type of coordinating moiety (e.g. an 5-sulfoisophthalate ligand).

The MOF may comprise more than one type of ligand.

The release of NO and, in some embodiment, one or more further biologically active agents, may be performed either inside an animal body, topically to an animal body or ex vivo in non-body applications such as release from surfaces such as clinical and food preparation sites.

The method may be applied to the treatment of humans or animals. Accordingly the present invention further provides as a further aspect a method of treatment or prophylaxis of an individual in need thereof comprising providing a MOF in accordance with other aspects of the invention, contacting the MOF with the individual and releasing NO (and optionally one or more further biologically active agents).

The NO (and/or further biologically active agent(s)) may be released from the pores and/or channels of the MOF.

The method may further comprise applying an external stimulus to the MOF. The external stimulus may be applied as a consequence of the physiological conditions (e.g. moisture, temperature) to which the MOF is exposed when contacted with the individual. The external stimulus may comprise, for example, irradiation with UV light. Thus, the method may comprise targeted release of NO (and/or the further biologically active agent(s)), by selectively applying an external stimulus—for example after a period of time has elapsed (e.g. sufficient for the MOF to by systematically distributed, or digested), and/or by exposing a particular region of the individual to the external stimulus (e.g. UV light).

According to a further aspect of the present invention, there is provided a metal organic framework material (MOF), comprising an extra-framework NONOate and/or N-nitroso compound within the internal pores and/or channels of the MOF (preferred and optional features of which correspond to those of other aspects of the invention), for use in surgery and/or therapy.

In another aspect, the invention extends to a pharmaceutical, neutraceutical or cosmetic preparation comprising a MOF comprising an extra-framework NONOate and/or N-nitroso compound within the internal pores and/or channels of the MOF together with a pharmaceutical/neutraceutical/cosmetic carrier therefor.

In a further aspect, the present invention provides the use of a metal organic framework material (MOF), comprising an extra-framework NONOate and/or N-nitroso compound within the internal pores and/or channels of the MOF, for the preparation of a medicament for use in the treatment or prophylaxis of disease.

Diseases or medical conditions which may be treated include infections of the skin, including dermatophyte fungi, leishmaniasis, molluscum and papilloma virus, and *mycobacterium* infections. Further uses include wound and/or burn healing. Therapies for other bacterial problems include the reduction of severe foot or body odour problems, and in the treatment of Methicillin Resistant *Staphylococcus Aureus* infections.

In yet another aspect of the invention there is provided a medical article comprising a MOF, the MOF comprising an extra-framework NONOate and/or N-nitroso compound within the internal pores and/or channels of the MOF.

Suitable medical articles for use in the present invention include stents, catheters, wound dressings, bandages, self-adhesive plasters and patches. For example, a fibre optic catheter may be impregnated with or coated with a NONOate and/or N-nitroso compound or a NONOate and/or N-nitroso-loaded MOF. Light, such as UV light may be transferred through the catheter by the optical fibre and this may trigger the release of NO.

The MOF may be provided in a coating of the medial article, for example as part of a paint, or polymeric coating. The MOF may be provided as a component of a material from which all, or a part of the medical article is made.

A MOF may for example be incorporated into a plastics formulation, which may in turn be moulded or formed into a fabric. The invention therefore also extends to a plastics composition comprising a MOF, the MOF comprising an extra-framework NONOate and/or N-nitroso compound within the internal pores and/or channels of the MOF.

The beneficial properties of the NO and, where applicable, further biologically active agent(s) may be advantageously employed in cosmetic and personal hygiene applications.

For example a MOF in accordance with aspects of the present invention may be used in cosmetic preparations; deodorants; skin preparations such as anti-aging skin preparations and preparations applied before, during or after hair removal by shaving or by application of depilatory preparations; hair preparations; depilatory preparations and the like.

Further preferred and optional features of each aspect of the invention correspond to preferred and optional features of any other aspect of the invention.

DESCRIPTION OF THE DRAWINGS

Non-limiting example embodiments will now be described with reference to the following figures in which.

DETAILED DESCRIPTION OF EXAMPLE EMBODIMENTS

Figure 1:
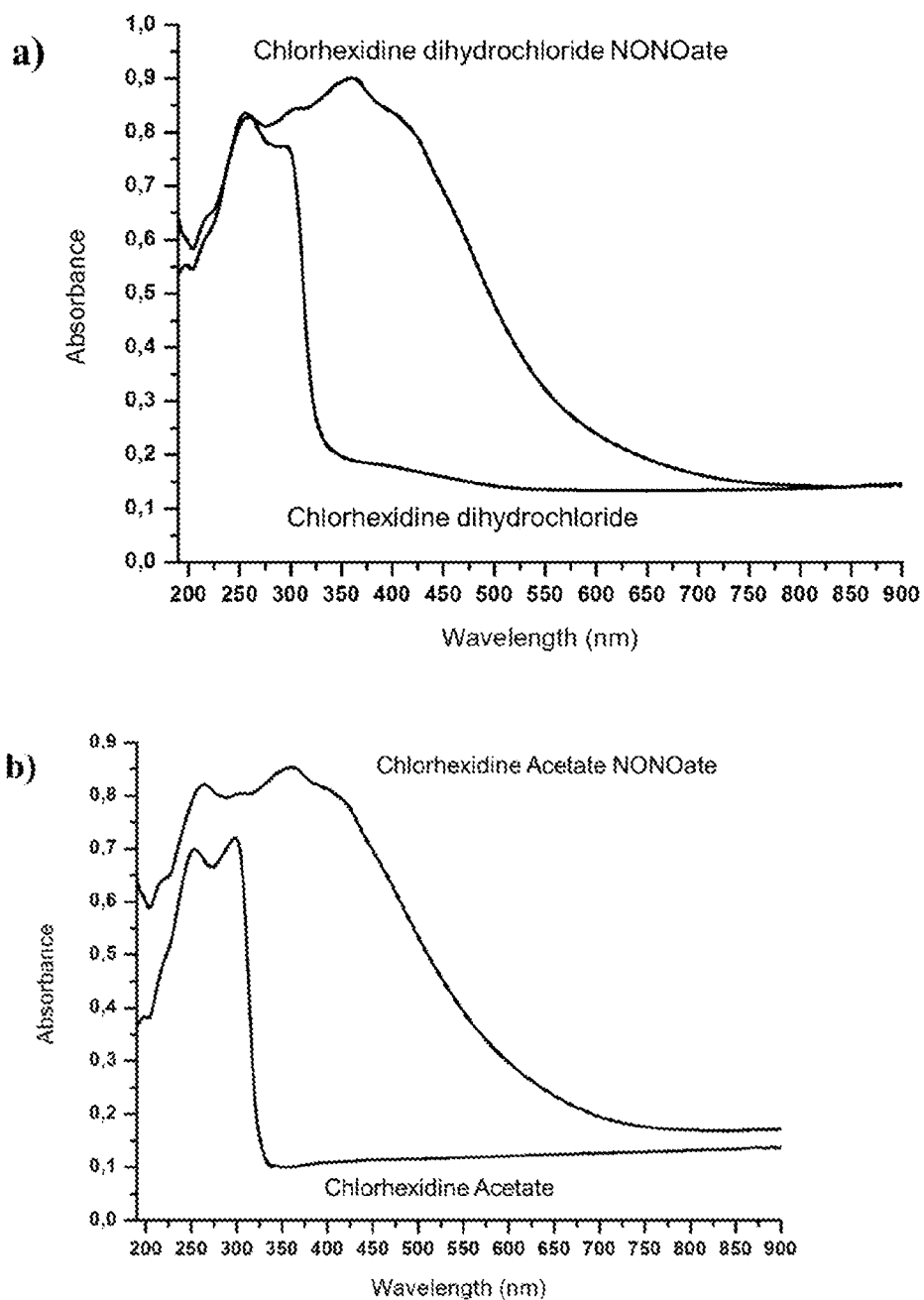
FIG. 1 shows UV-visible spectra of chlorhexidine dichloride and chlorhexidine diacetate before and after NO loading.

Preparation and Release of NO from Chlorhexidine NONOate and/or N-Nitroso Compounds Chlorhexidine is reported on the World Health Organization's List of Essential Medicines. This pharmaceutical product is widely used in disinfectants (for external use on skin and hands) and topical use (preservative in eye drops, active substance in wound dressings and antiseptic mouthwashes). Furthermore this biomolecule can also be found in cosmetics (additive to creams, toothpaste and deodorants). This drug is primarily sold as salts (dihydrochloride, diacetate and digluconate). Recently, different chlorhexidine-metal complexes have been reported; the drug binds to specific metals (like copper and silver) providing a system for the controlled release of chlorhexidine, while maintaining the drug performance [1].

Chlorhexidine contains primary and secondary amine groups. The inventors have found that these amine groups are capable of binding NO when exposed to nitric oxide gas under high pressure.

In addition, the release of NO from chlorhexidine may be triggered by ultra-violet light (UV) or exposure to humidity. Indeed, NO release can be triggered by either or both of these external stimuli. As detailed below, after an initial burst caused by exposure to humidity, the NO release can be repeatedly triggered and stopped by switching the source of UV light on and off.

Advantageously and unexpectedly, the chlorhexidine NONOate and/or N-nitroso compounds have been found to be stable in air, meaning no special storage conditions are necessary.

Light-controlled release is possible from a number of different chlorhexidine salts. The combination of chlorhexidine and NO has a synergistic effect, which reduces the risk of potential bacterial resistance and can be useful in combatting already resistant strains of microbes.

A benefit of a chlorhexidine-NONOate/N-nitroso compound is that the chlorhexidine precursor which is regenerated after NO release is a well understood and beneficially biologically active agent. Moreover, appropriate dosages, side effects and toxicity are well understood.

(1) Formation of and NO Release from Chlorhexidine-NONOate and/or N-Nitroso and Complexes and M-Chlorhexidine-NONOate and/or N-Nitroso Salts Chlorhexidine, its salts and complexes (precursor compounds) may be converted to their NONOate and/or N-nitroso compound using the high temperature dehydration and NO loading technique previously reported by Morris [2], in relation to MOF and zeolite materials.

The chlorhexidine-NONOate and/or N-nitroso compounds may also be prepared generally as outlined by Lowe at al. [17] in which the material is subjected to high vacuum at approximately room temperature before being exposed to NO atmosphere.

These techniques have previously only be considered for use in loading MOF and other molecular sieve materials with NO, so that the NO adsorbs to framework ions or ligands. Such methods have not previously been applied to "free" NONOate and/or N-nitroso precursor compounds.

Any chlorhexidine salt can be employed as a starting material, as demonstrated in relation to chlorhexidine diacetate, chlorhexidine dihydrochloride and chlorhexidine digluconate.

The identity of the chlorhexidine precursor may be selected in for a preferred NO release profile. The inventors have observed that the release profile on exposure of the NONOate and/or N-nitroso compound to humidity is particularly sensitive to the particular precursor which has been selected.

For example, if a large initial "burst" of NO on contact with humidity or moisture is desired, then chlorhexidine dihydrochloride salt may be appropriate, for example.

Whereas, the chlorhexidine diacetate salt has a more gradual release profile on exposure to humidity/moisture.

The formation of NONOates and/or N-nitroso compounds has also been demonstrated for metal-chlorhexidine complexes. M-chlorhexidine NONOate and/or N-nitroso complexes have been formed by solvothermal/hydrothermal synthesis and mechanochemical synthesis. A preferred method is generally via the low temperature process reported by Morris at al. [23]. Again, this low temperature process has only previously been used to prepare MOF materials.

The metal employed can be any metal but preferably those with antimicrobial properties such as Ag, Ni, Zn and Cu. These metals themselves have biological (e.g. antibacterial) activity and provide the NONOate and/or N-nitroso salt/complex with a still further mode of action (in addition to the activity and/or release profile of the NO and the chlorhexidine anion).

In addition to release of NO by exposure to humid air, moisture or UV-light, NO release may also be initiated or stimulated by heating the chlorhexidine NONOate compound.

It is a particular feature of these materials that a combined release trigger can be used to afford an initial burst followed by sustained release.

Example 1—Chlorhexidine Diacetate and Dihydrochloride NO Loading

A sample of 50 mg of chlorhexidine diacetate hydrate and chlorhexidine dihydrochloride were exposed to high vacuum ($10^{-4}$ Torr) for 1 hour at room temperature. Using a schlenk line, 4 atmospheres of NO gas were introduced into the schlenk tube over 2 hours allowing the dehydrated chlorhexidine to adsorb the radical gas. The samples were then exposed to vacuum and flushed with argon for 30 minutes. The glass vials containing the samples were then sealed.

FIG. 1 shows the detected UV Vis-spectra of the pure chlorhexidine compared to the NO containing complex. The exposure of the drug to the nitric oxide gas changes the colour of the material from white to pale yellow. The UV data indicates a change in the absorbance band at ~370 $cm^{-1}$ for both the chlorhexidine dihydrochloride and diacetate NO complexes. This is consistent with literature reports for other NO containing materials[16].

The nitric oxide adsorption/desorption profiles for two further chlorhexidine diacetate samples (25 mg) were collected using a bespoke gravimetric adsorption system. Each sample was exposed to high vacuum at a pressure of $1 \times 10^{-4}$ mbar overnight until no further mass loss was observed. The samples were cooled to 298K using a water bath (temperature accuracy of 0.02K).

Figure 2:
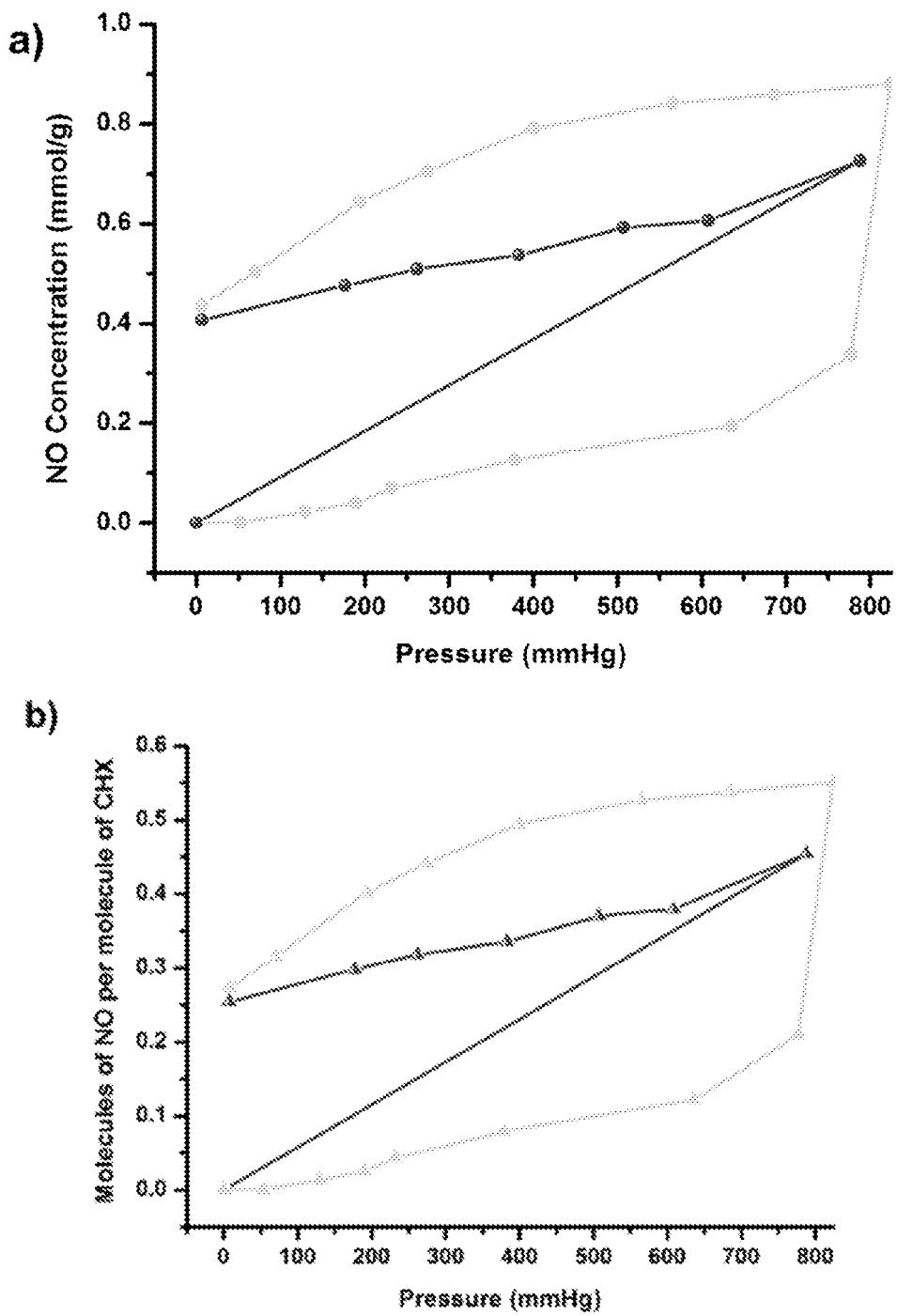
FIG. 2 shows adsorption (-■-) and desorption (-□-) isotherms of NO at 298K (measured using gravimetric analysis) for each of two samples of chlorhexidine diacetate plotted as (a) nitric oxide concentration (mmol/g) and (b) molecules of nitric oxide per molecule of chlorhexidine.

For one sample, shown in the outer plot of FIGS. 2(a) and (b), NO was introduced in increasing increments. After each dose of NO, the mass of the sample was allowed to stabilise (indicating completion of adsorption) before the next addition was made. This process was continued until the introduced pressure of NO was equal to atmospheric pressure. The second sample was exposed to one atmosphere of NO in a single step, and its mass allowed to equilibrate. Data is shown in the inner plot of FIGS. 2(a) and (b). The desorption profiles of both samples, shown in FIGS. 2(a) and 2(b), were measured by reducing the pressure in increments to a final value of $2 \times 10^{-2}$ mbar.

The gravimetric analyses show that a maximum of ~0.9 mmole of NO per gram are adsorbed (FIG. 2a) which equates to 0.55 molecules of NO per molecule of chlorhexidine (FIG. 2b).

The shape of the adsorption curve shows a dependence between the applied pressure of NO and the quantity of NO bonding to the molecule. The pressure of NO normally used for the loading on the schlenk line is 4 times the level obtainable during the gravimetric isotherm analysis, so we would expect an even higher quantity of radical gas coordinating to chlorhexidine. Through reapplication of vacuum the NO levels reduce progressively, and both samples reach a level of stored NO of ~0.4 mmole per gram, circa 0.25 molecules per molecule of chlorhexidine. These data indicate that a significant proportion of the NO initially stored has been adsorbed by the chlorhexidine precursor.

The release of NO from the sample was first triggered by passing a constant flow of humid nitrogen gas (11% RH) over it. The amount of NO released over time was detected using a Sievers NOA 280i chemiluminescence nitric oxide analyser until the emission of NO reached a level lower than 20 ppb.

Figure 3:
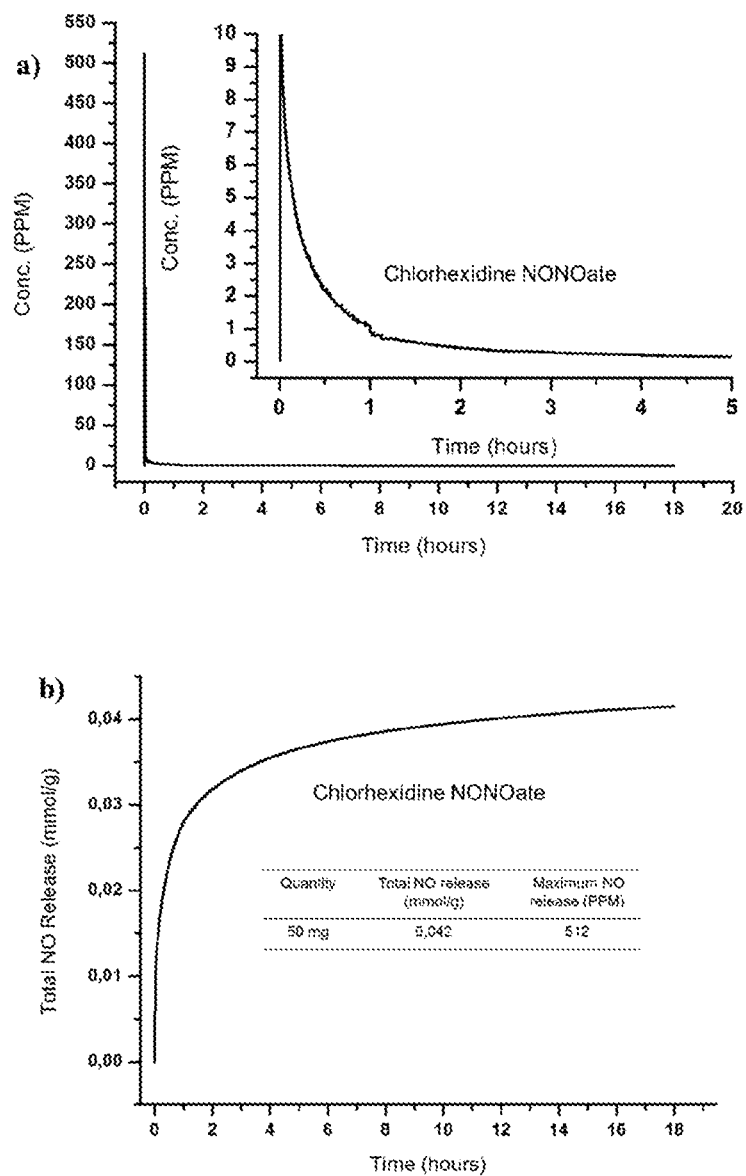
FIG. 3 shows chemiluminescence analysis of nitric oxide delivery from chlorhexidine diacetate on contact with humid atmosphere (11% RH). Plotted data of concentration of NO over time (FIG. 2a) and total NO release over time (FIG. 2b)

The initial burst of release of NO reached 512 PPM (FIG. 3). The sample released up to 0.042 mmol/g of nitric oxide in 19 hr.

After the NO release was completed the sample was kept on the bench at room temperature, exposed to air and humidity for over 48 hr. The sample was exposed to UV light from two Ritek Electronics UV tube lamps each containing 4×15 W bulbs with an emission of 300-400 nm and total power of 50-200 W. These parameters should not be viewed as limiting with regards to the invention. The light triggered NO release that immediately burst from 30 to 105 ppb. A maximum of around 120 ppb was reached on continuous exposure for about 5 mins.

Figure 4:
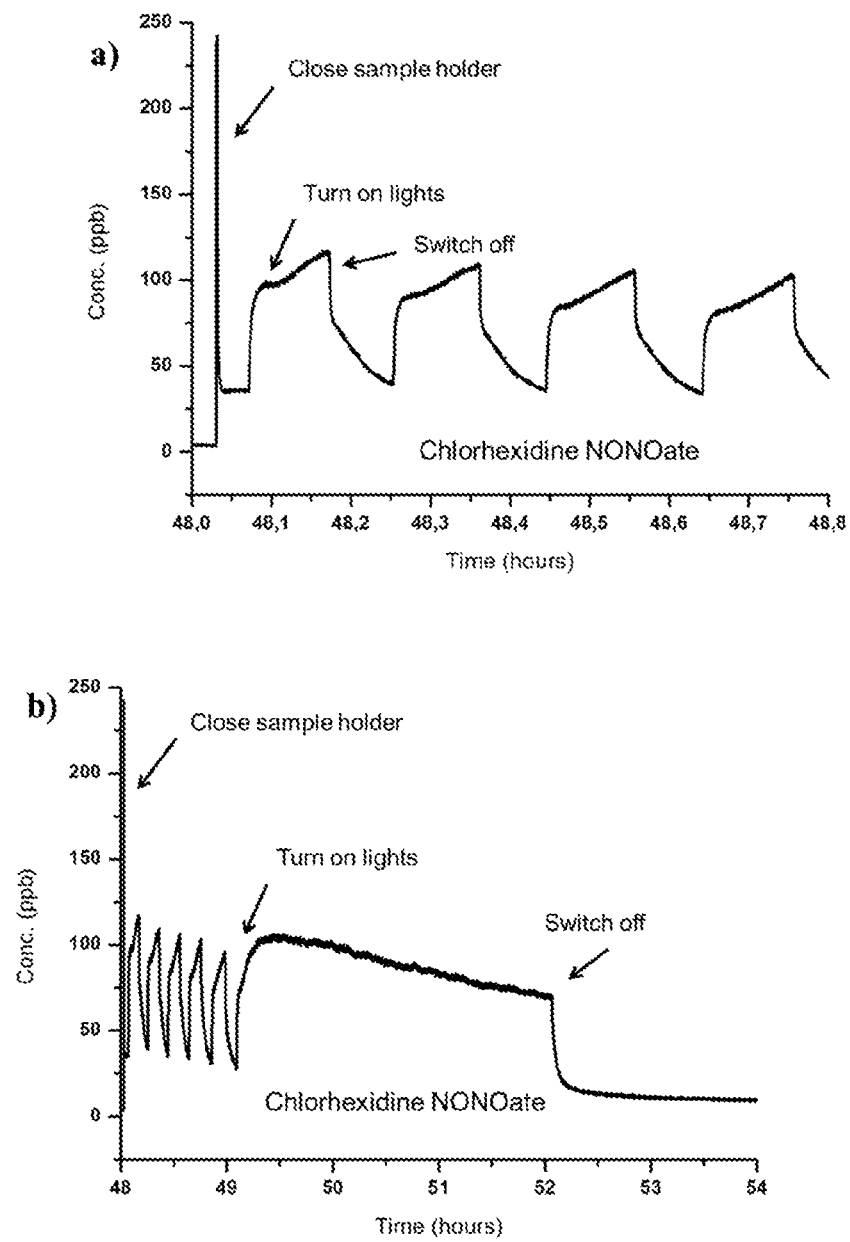
FIG. 4 shows chemiluminescence analysis of total Nitric Oxide delivery from chlorhexidine diacetate, in contact with humid atmosphere (11% RH), triggered by UV light. The sample was kept in a vial for 48 hours at room temperature and expose to air prior to irradiation.

The emission immediately stopped when the source of UV light was switched off as shown in FIG. 4a. This on-off process can be repeated and controlled over time. Continuous exposure to UV light triggers a release of nitric oxide over 70 ppb for more than 4 hrs, as shown in FIG. 4b. The release of NO over time was recorded using the same analyser described above.

Example 2—NO Release from Chlorhexidine NO Complex Suspended in Water

A 100 mg sample of chlorhexidine diacetate was exposed to high vacuum ($10^{-4}$ Torr) for 12 hours at room temperature. Using a schlenk line, 4 atmospheres of NO gas were introduced into the schlenk tube and maintained for 2 hours allowing the dehydrated chlorhexidine to adsorb the gas. The sample was then exposed to vacuum and flushed with argon for 30 minutes. The glass vials containing the sample were then sealed.

The NO-loaded sample was submersed under 5 ml of deionized water in a sealed chamber connected to an NO analyser. A constant flow of nitrogen was bubbled through the suspension while measuring the concentration of NO present in the chamber atmosphere.

Figure 5:
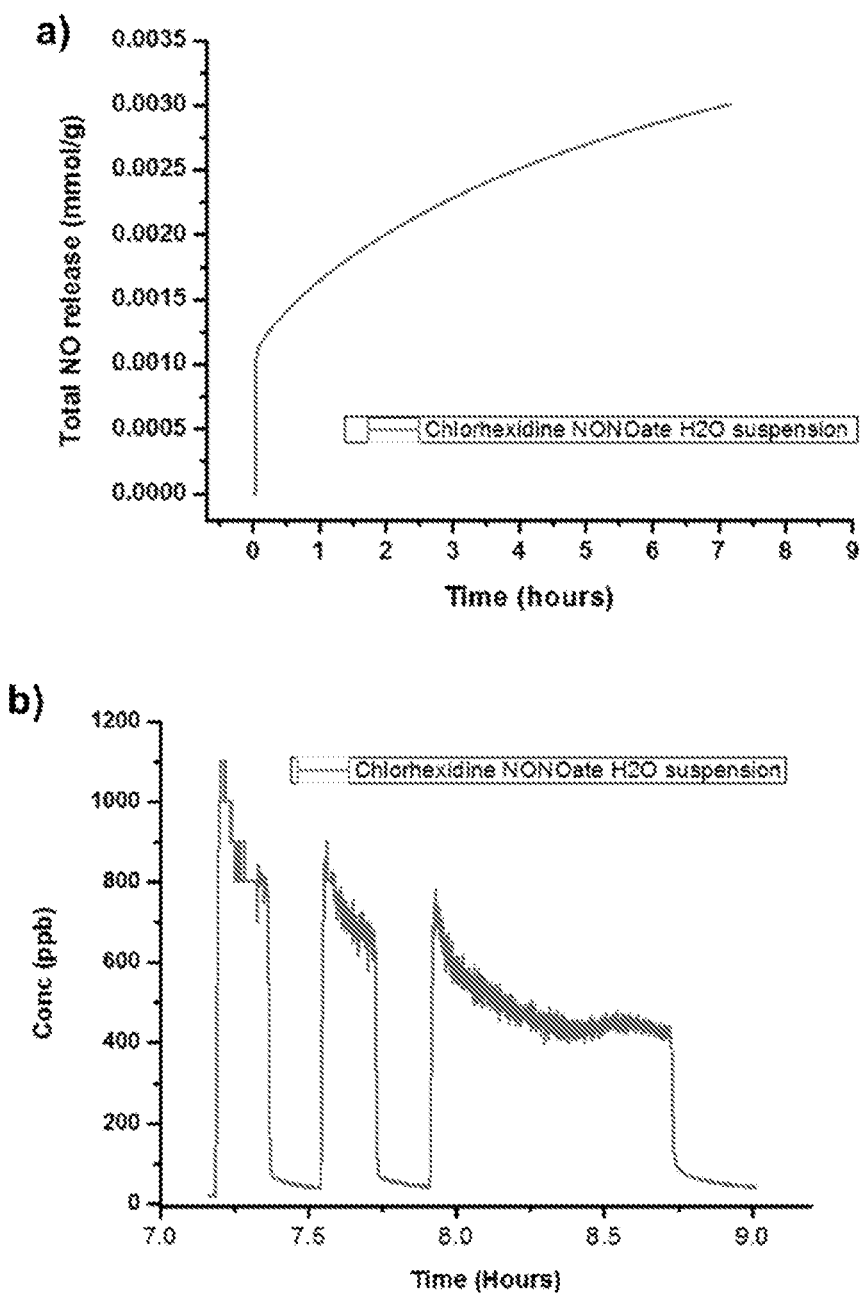
FIG. 5 shows chemiluminescence analysis of nitric oxide delivery from chlorhexidine NO complex in water (100% RH) (FIG. 5a) and triggered by UV light (FIG. 5b)

The release of NO from the sample triggered by the water was measured in ppm and ppb over time until the level of NO dropped below 20 ppb. The initial burst release of NO reached 40 ppm. The sample released up to 0.035 mmol/g of nitric oxide in 7 hrs (FIG. 5a).

Immediately after the NO release was completed the sample was exposed to UV light, which triggered further release of NO. A maximum of around 1000 ppb was recorded during continuous exposure for about 10 minutes. The emission immediately stopped when the source of UV light was switched off as shown in FIG. 5b. This on-off process can be repeated and controlled over time.

Example 3—Chlorhexidine Dihydrochloride NO Loading and Release

Figure 6:
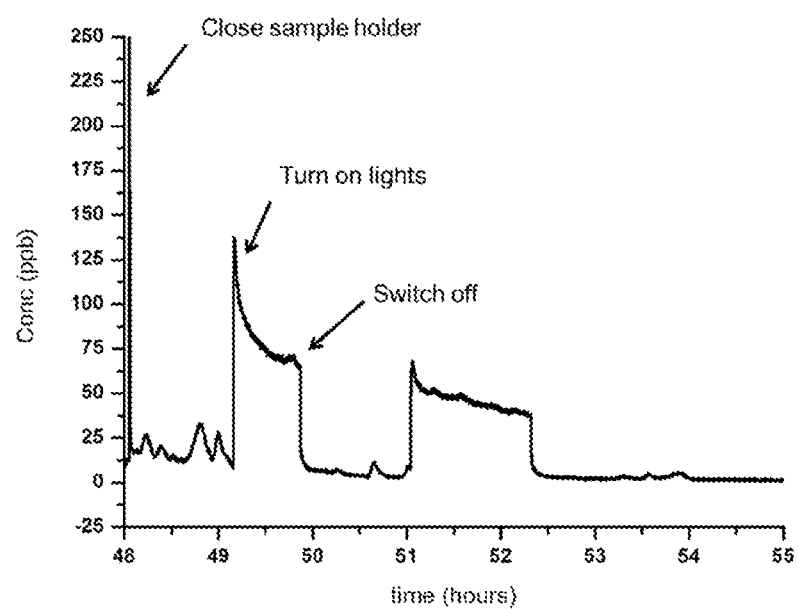
FIG. 6 shows chemiluminescence analysis of Nitric Oxide delivery from chlorhexidine dichloride, in contact with humid atmosphere (11% RH), triggered by UV light.

The same general process described above was followed using chlorhexidine dihydrochloride as starting material. An initial burst release of NO was obtained on exposing the sample to a constant flow of humid nitrogen gas (11% RH). The material released a small amount of gas for a couple of minutes and then stopped. After storing the sample on the bench, exposed to humid air for 2 days, an additional release of NO was triggered using UV light. Chlorhexidine dihydrochloride releases a burst of NO up to 150 ppb dropping to 75 ppb over 1 hr. This trigger mechanism can be repeated and controlled over time as shown in FIG. 6.

Example 4—NO Loading and Release from a Silver-Chlorhexidine Complex

Following the procedure of Song a sample of silver-chlorhexidine was prepared using silver nitrate and chlorhexidine diacetate. After characterisation (XRD, UV Vis, SEM and EDX) 50 mg of the sample were loaded with NO following the high pressure procedure previously reported [17].

Figure 7:
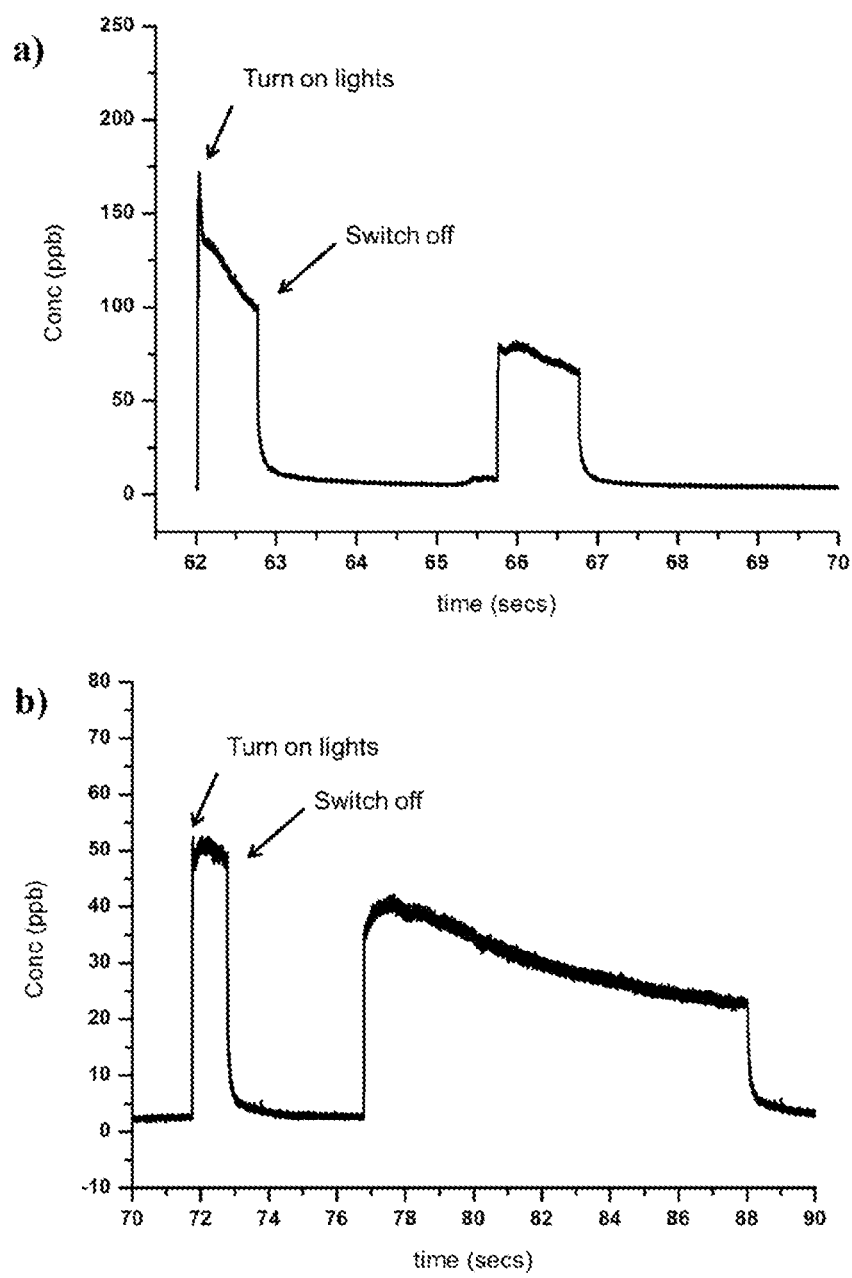
FIG. 7 shows chemiluminescence analysis of total nitric oxide delivery from chlorhexidine diacetate silver metal complex, in contact with humid atmosphere (11% RH), triggered by UV light.

The initial burst release of NO, triggered by exposing the sample to humidity, lasted for a couple of minutes. The sample was stored exposed to humid air for over 60 hrs before an additional release of nitric oxide was triggered using UV light as shown in FIG. 7.

The silver chlorhexidine complex released a burst of NO (up to 175 ppb) that slowly dropped to 100 ppb over the course of an hour. As in the cases above, the release of NO stopped abruptly when the UV light was switched off. This trigger mechanism can be repeated and controlled over time as shown in FIG. 7a. The NO release can be switched on and off multiple times even after 85 hrs as shown in FIG. 7b.

Example 5—NO Release from Polymer Film Containing NO-Complexed Chlorhexidine Diacetate A polyurethane polymer was chosen as a casting material as it is commonly used in medical devices. A sample of chlorhexidine diacetate (1.5 g) was dispersed in a predissolved mixture of polyurethane (3 g) and THF (40 ml). The mixture was solvent cast using doctor blade techniques, to produce a ~100 μm thick film, which was set by evaporation of the solvent.

Samples of the polymer film were exposed to vacuum overnight and NO loaded using two different pressures (1 bar and 4 bar) of nitric oxide.

Figure 8:
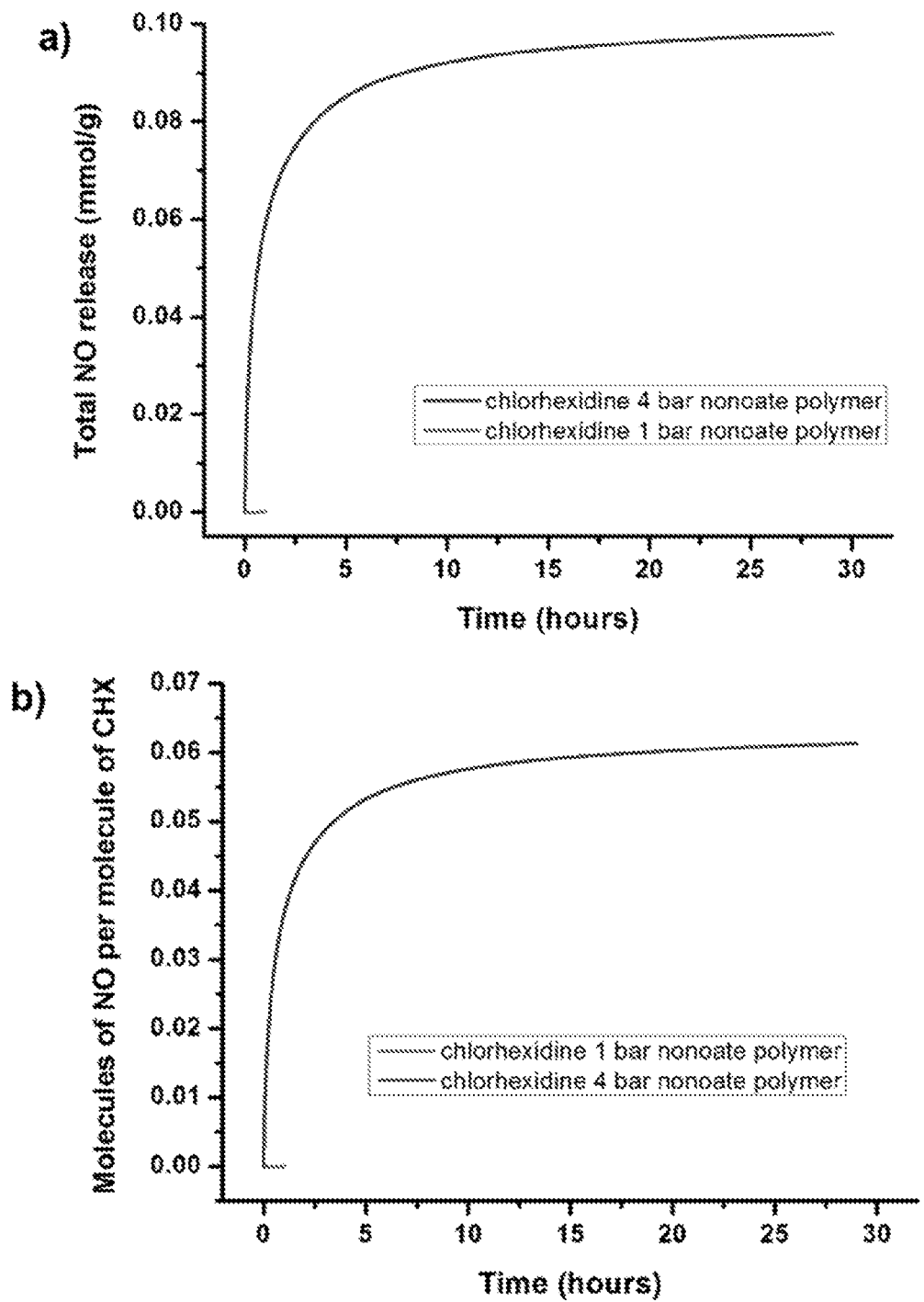
FIG. 8 shows total NO release (measured using chemiluminescence analysis) on contact with humid atmosphere (11% RH), plotted as (a) mmole per gram and (b) molecules of NO per molecule of chlorhexidine (CHX) over time, from polymer cast chlorhexidine loaded with NO at 4 bar (blue), and of polymer cast chlorhexidine loaded with NO at 1 bar (red)

FIG. 8 shows NO release profiles (chemiluminescence analysis), using humid nitrogen only (humidity controlled 11% RH), of 100 mg samples of the NO-loaded chlorhexidine-containing films, loaded at 4 bar and 1 bar. The data show that the sample loaded at 4 bar releases up to 0.1 mmole per gram of nitric oxide within a 30 hour time period (FIG. 8a), which equates to 0.06 molecules of NO per molecule of chlorhexidine (FIG. 8b).

It has also been found that polymer-cast chlorhexidine loaded with NO at 1 bar does not release any NO under analogous conditions (as also shown FIG. 8).

Example 6—UV Triggered NO Release from Polymer-Cast NO-Complexed Chlorhexidine Diacetate After the initial NO release was completed by exposing the samples to humid nitrogen, the samples were stored on the bench at room temperature, exposed to air and humidity for over 48 hrs. Both samples were then exposed to UV light in a flow of humid nitrogen gas (humidity controlled 11% RH).

This triggered additional release of NO from the samples, including the film that had been loaded with NO at 1 bar, in direct contrast to its performance in solely humid nitrogen. A maximum of around 180 ppb was reached on continuous exposure for about 10 minutes from this sample.

Figure 9:
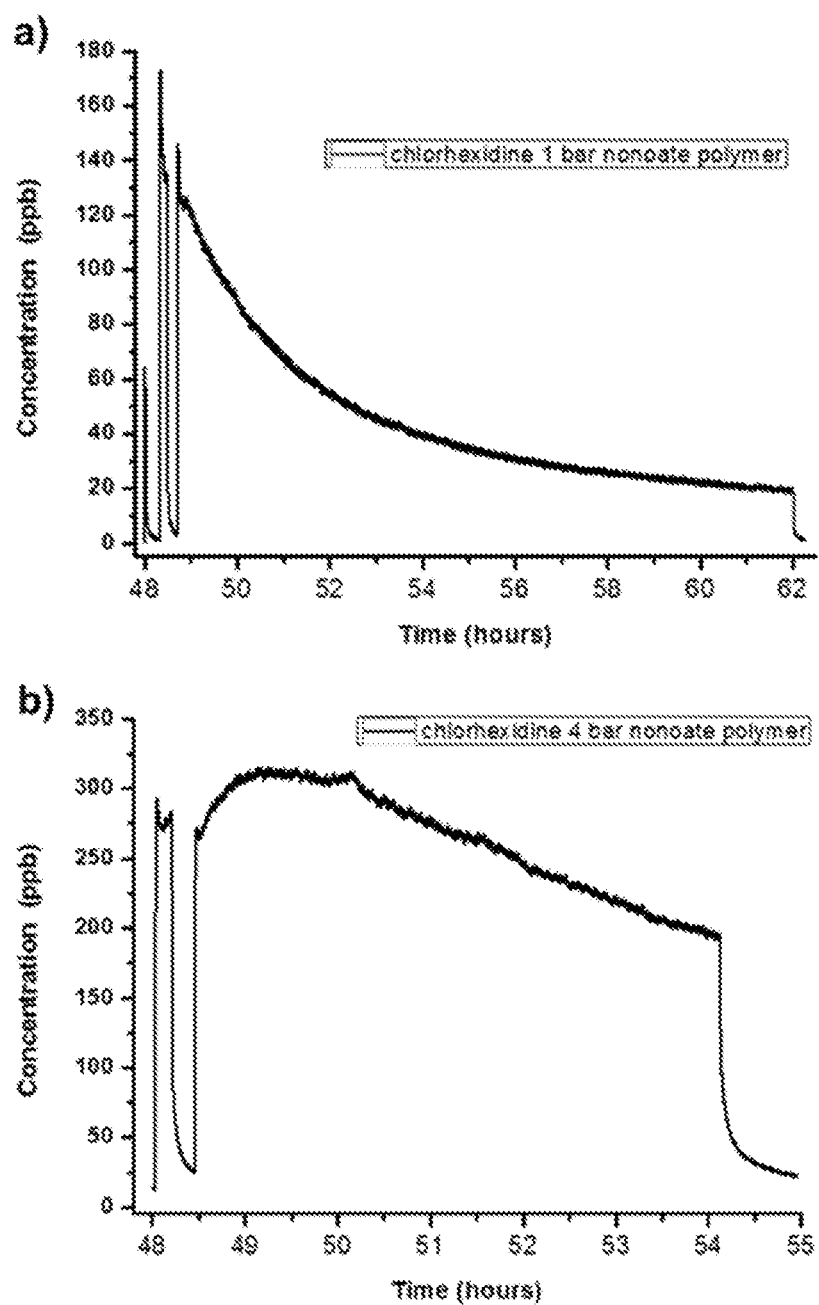
FIG. 9 shows chemiluminescence analysis of nitric oxide delivery from (a) polymer cast chlorhexidine loaded with NO at 4 bar and (b) polymer casted chlorhexidine loaded with NO at 1 bar, each in contact with humid atmosphere (11% RH), triggered by UV light.

The emission immediately stopped when the source of UV light was switched off as shown in FIG. 9a. This on-off process can be repeated and controlled over time. Continuous exposure to UV light triggered a release of nitric oxide over 20 ppb for more than 14 hrs, as shown in FIG. 9a.

Figure 10:
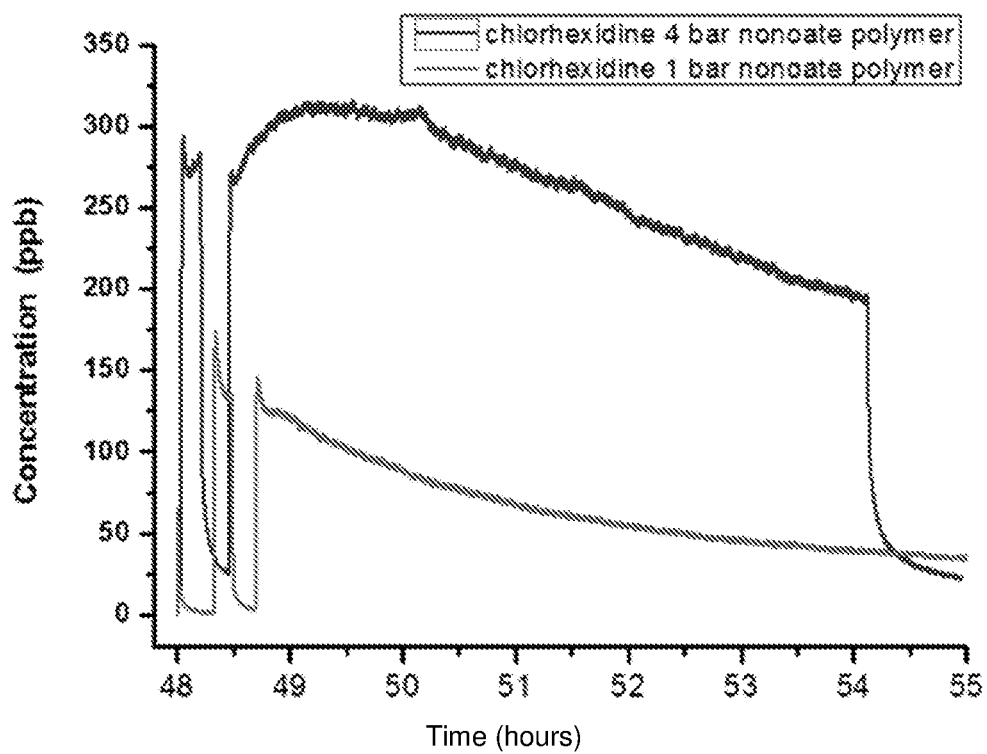
FIG. 10 shows chemiluminescence analysis of nitric oxide delivery triggered by UV light from polymer cast chlorhexidine loaded with NO at 4 bar (upper, blue plot) and at 1 bar (lower, red plot) in contact with humid atmosphere (11% RH)

The chlorhexidine-containing polymer sample that had been loaded with NO at 4 bar released almost twice the amount obtained from the 1 bar counterpart as shown in FIG. 10. The pressure of NO used during the gas-loading process therefore significantly influences the final release performance obtained from the sample, using only water and/or UV-light as a trigger. A maximum of around 300 ppb was reached from this sample on continuous exposure for about 10 minutes as shown in FIG. 9b. The emission immediately stopped when the source of UV light was switched off. This on-off process can be repeated and controlled over time.

(2) Formation of and NO Release from NO-Complexed Ciprofloxacin Compound

It has been found that the process described above can be used on different drugs containing secondary amines in their structure, such as ciprofloxacin. Ciprofloxacin is an antibiotic useful for the treatment of different bacterial infections.

Example 7

Figure 11:
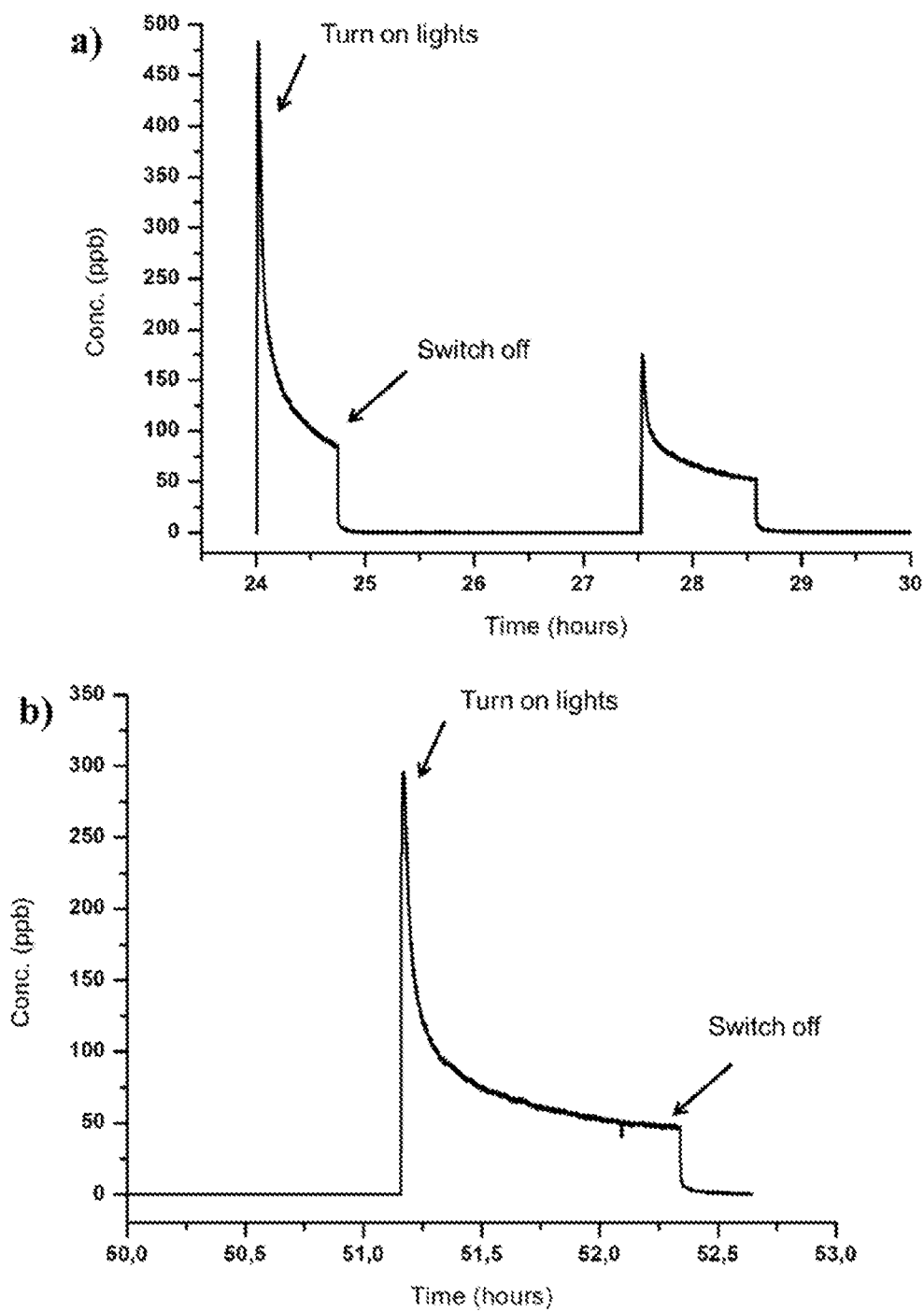
FIG. 11 shows chemiluminescence analysis of Nitric Oxide delivery from ciprofloxacin, in contact with humid atmosphere (11% RH), triggered by UV light.

50 mg of ciprofloxacin was NO loaded following the high pressure method reported above. A small initial burst of nitric oxide, lasting a couple of minutes, was obtained after exposure to a constant flow of humid nitrogen gas (11% RH). However, even after storing the sample on the bench exposed to humid air for 24 hrs, an additional release of NO was triggered using UV light. Ciprofloxacin released a burst of NO up to 500 ppb dropping to around 100 ppb over 1 hr. The mechanism can be repeated over time and controlled as shown in FIG. 11a. After keeping the sample exposed to humid air for over 50 hrs additional NO was still released using UV light as a trigger as shown in FIG. 11b. The burst of NO release reached 320 ppb dropping to 50 ppb over 1.5 hrs.

FT-IR-Analyses

Figure 12:
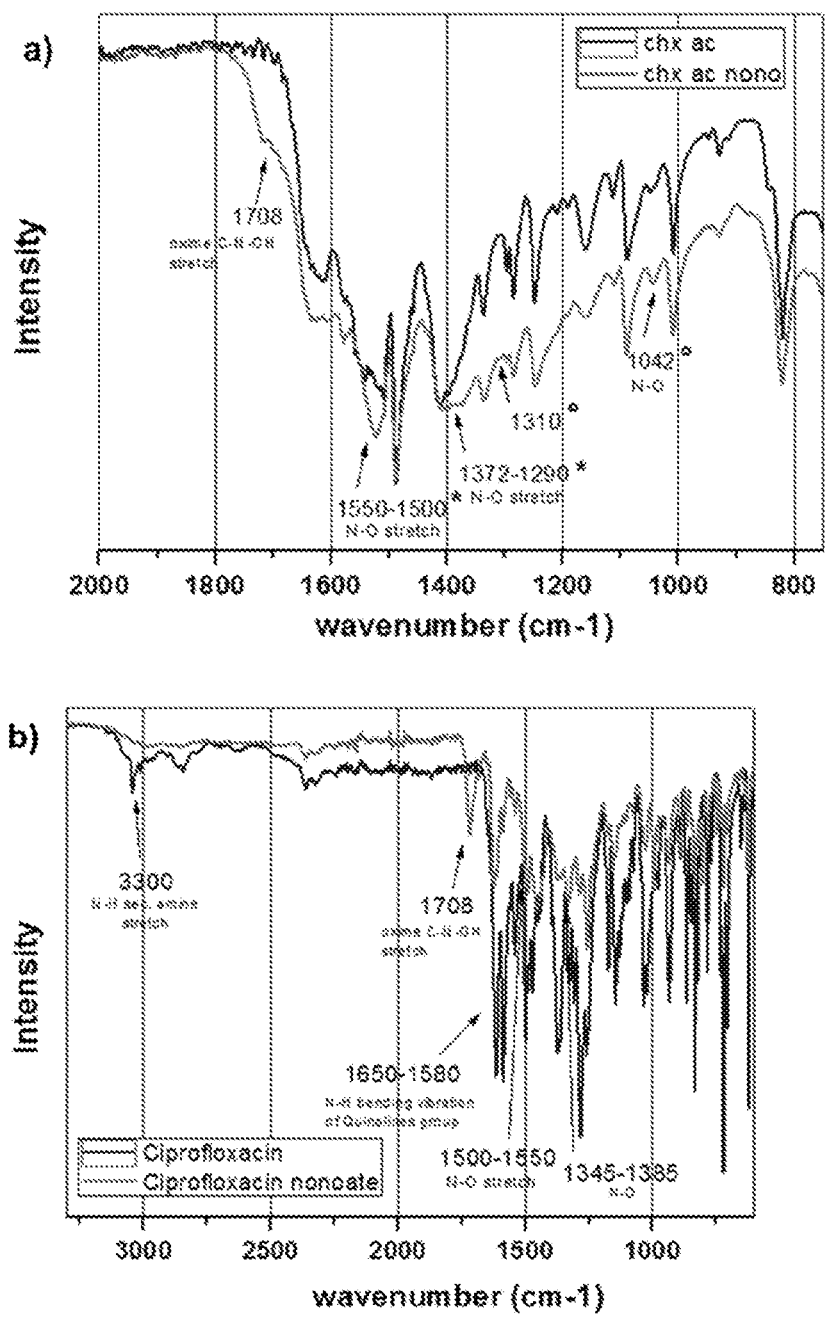
FIG. 12 shows FT-IR spectra of (a) chlorhexidine diacetate before (blue) and after (red) exposure to NO and of (b) ciprofloxacin before (blue) and after (red) exposure to NO.

Evidence for the attachment of NO to the ciprofloxacin molecule is provided by the appearance of new stretching frequencies in the FT-IR spectra for both samples after exposure to NO (FIG. 12); for example, the stretching frequencies at 1040-1043 cm$^{-1}$ (N-O) (FIG. 12a), 1310-1320 cm$^{-1}$ (N-O) (FIG. 12a, b) and 1550-1500 cm$^{-1}$ (N-O) (FIG. 12a, b). There is also an additional stretching band; 2270-2275 cm$^{-1}$ present in all NO-modified compounds, which is most likely due to an N-N stretch.

There is also a small stretch above 1700 cm$^{-1}$ present in each of the NO complexed compound samples. Although the origin of this stretch is not fully understood, it has been found to be present in other literature-reported spectra of NO-containing compounds (see for example J. G. Nguyen, Kristine K. Tanabe and S. M. Cohen Cryst. Eng. Comm, 2010, 12, 2335-2338). Furthermore, FIG. 11b also shows the disappearance of the NH stretch at 3300 cm$^{-1}$ when ciprofloxacin is exposed to NO.

(3) Furosemide

Furosemide is a loop diuretic used in the treatment of congestive heart failure and edema. Along with some other diuretics, furosemide is also included on the World Anti-Doping Agency's banned drug list due to its alleged use as a masking agent for other drugs. It is also on the World Health Organization's List of Essential Medicines, a list of the most important medication needed in a basic health system.

Furosemide is primarily used for the treatment of hypertension and edema. It is the first-line agent for most people with edema caused by congestive heart failure. It is also used for hepatic cirrhosis, renal impairment, nephrotic syndrome, and in the management of severe hyperkalemia in combination with adequate rehydration Example 8—Furosemide NO Loading and Release 25 mg of furosemide was exposed to high vacuum ($10^{-4}$ Torr) for 1 hour at room temperature. Using a schlenk-line, 4 atmospheres of NO gas were introduced into the schlenk tube and maintained for 2 hours allowing the dehydrated furosemide to adsorb the gas. The sample was then exposed to vacuum and flushed with argon for 30 minutes. The glass vials containing the samples were then sealed.

The release of NO was first triggered by passing a constant flow of humid nitrogen gas (11% RH) from the sample. The amount of NO released over time was detected in ppm and ppb until the emission of NO dropped below 20 ppb.

Figure 13:
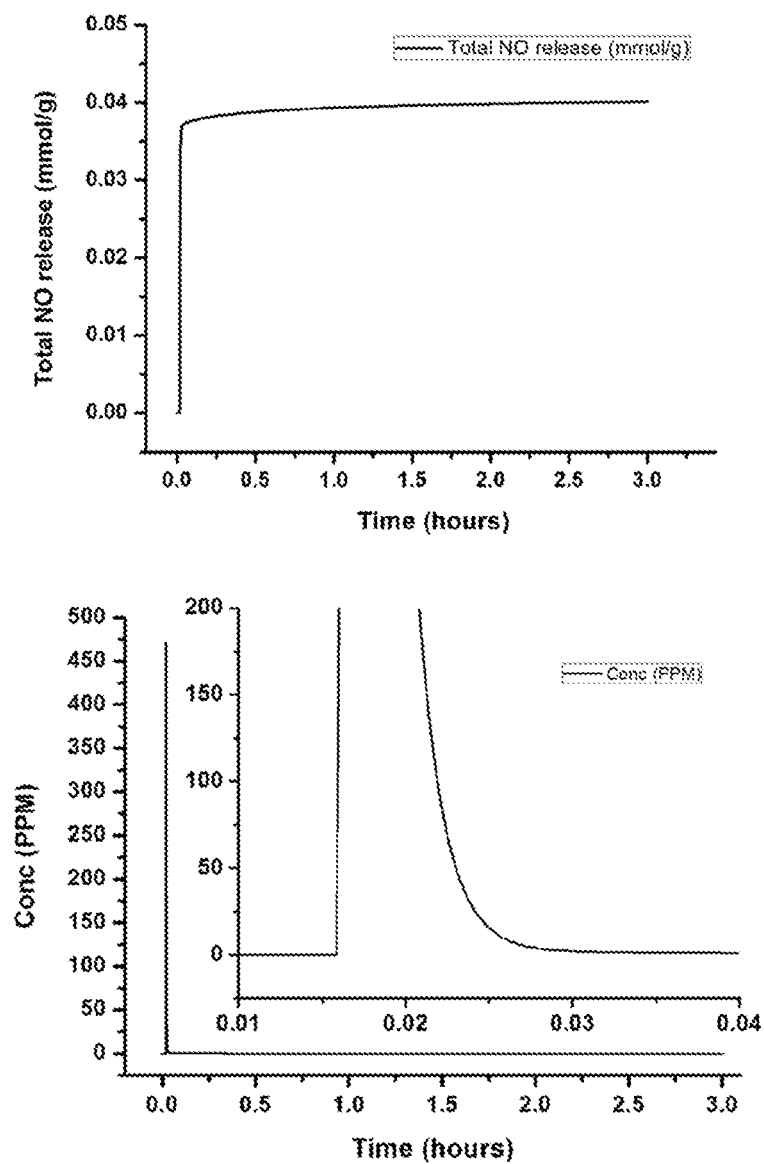
FIG. 13 shows total NO release (measured using chemiluminescence analysis) from furosemide on contact with humid atmosphere (11% RH) (plotted as mmole per gram)

The initial burst of release of NO reached 512 ppm (FIG. 13). The sample released up to 0.042 mmol/g of nitric oxide in 19 hrs.

Example 9—UV Triggered NO Release from Furosemide NO Complex

After the initial NO release by humid nitrogen was completed the sample was stored on the bench at room temperature, exposed to air and humidity for over 24 hrs. The sample was then exposed to UV light in a flow of humid nitrogen gas (humidity controlled 11% RH).

Figure 14:
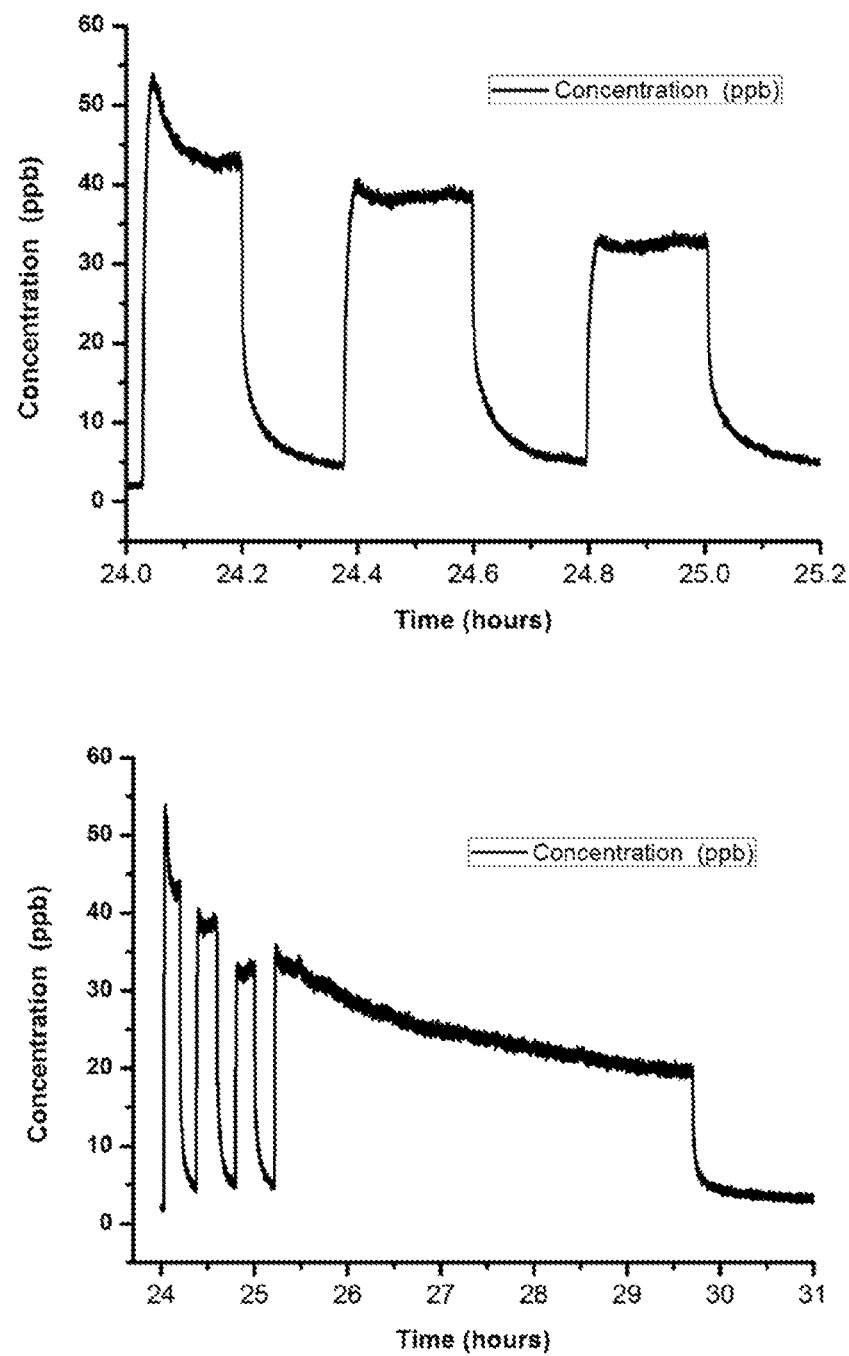
FIG. 14 shows chemiluminescence analysis of nitric oxide release from furosemide in contact with humid atmosphere (11% RH), triggered by UV light.

A maximum of around 55 ppb was reached on continuous exposure for about 10 minutes from the furosemide NONO-ate sample. The emission immediately stopped when the source of UV light was switched off as shown in FIG. 14.

This on-off process can be repeated and controlled over time. Continuous exposure to UV light triggered a release of nitric oxide over 20 ppb for more than 7 hrs.

(4) Light Triggered NO Release from MOFs

UV light-triggered NO release from MOFs has been demonstrated for CPO-27 and HKUST-1 type structures amongst others (in particular other MOFs having coordinatively unsaturated framework metal sites). However, the technique can be applied to any MOF that shows affinity for NO.

The MOFs were prepared following the method previously reported by Morris [23]. The activation and NO loading was carried out in accordance with the high temperature dehydration method previously reported by Morris [2,8]. However, NO-loading may be performed by any suitable method, for example as described by Lowe [17], in which the material is subject to a vacuum at room temperature before being exposed to a high pressure of nitric oxide.

The MOF may be selected for a desired NO release profile. For example Mg and Ni-CPO-27 tend to release higher quantities of NO than HKUST-1.

Release of the adsorbed NO is triggered by exposing the material to UV light. Alternatively, or in addition, NO release can also be achieved on exposure to humid air and/or heat.

For example, in some case an initial NO burst can be triggered by contact with moisture and, once the release of nitric oxide dissipated, UV light can be used to selectively trigger the release of additional NO by switching the UV light source on and off.

In this particular method may provide for release of a greater amount or proportion of the stored NO than has been previously possible. Although not wishing to be bound by theory, this may be a consequence of the UV light triggering the release of more strongly bonded (high energy) NO, which would not ordinarily be released by being displaced by water, or under thermal conditions conventionally applied. The UV triggered release of NO has particular use with MOFs that show poor NO release when exposed exclusively to humidity (eg. CPO-27 Mg and HKUST-1). Such materials are known to have relatively high NO storage capabilities, which it has not previously been possible to readily release.

Example 10—CPO-27 Mg

A sample of 50 mg CPO-27 Mg prepared following the procedure reported by Morris [23] was exposed to high vacuum ($10^{-4}$ Torr) for 1 hr at room temperature. The sample was then exposed to 4 atm of NO gas for 2 hr before being evacuated and flushed with argon for 30 minutes and sealed in glass vials.

Figure 15:
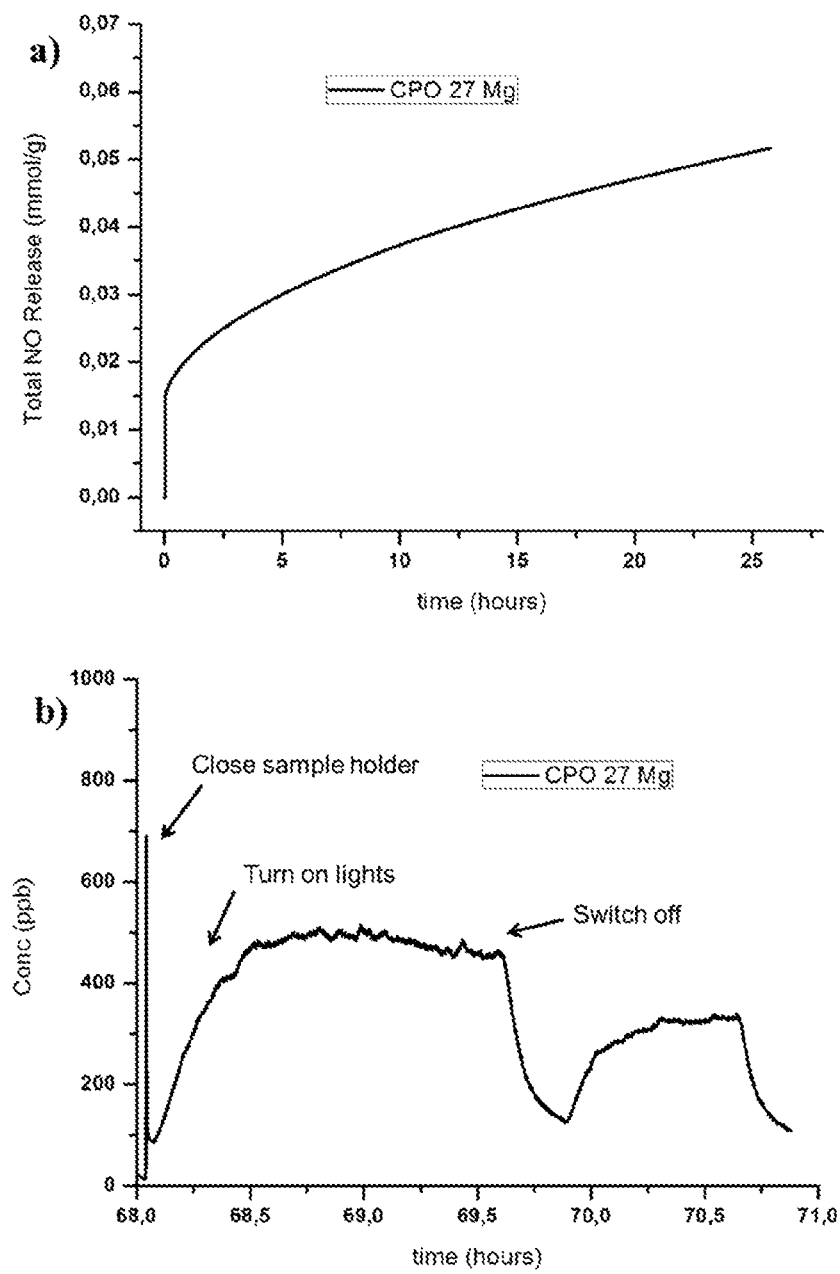
FIG. 15 shows chemiluminescence analysis of total nitric oxide delivery from CPO 27 Mg on contact with humid atmosphere (11% RH) FIG. 7a. NO release from CPO 27 Mg, in contact with humid atmosphere (11% RH), triggered by UV light FIG. 7b. The sample was stored on the bench at room temperature exposed to air and humidity for over 68 hours in between the two analyses.

Total NO release: The sample was exposed to a constant flow of humid nitrogen gas (11% RH) and the NO released was monitored over time. The analysis was carried out until the NO gas levels detected were lower than 20 ppb. CPO-27 Mg only released up to 0.05 mmol/g over 25 hrs as shown in FIG. 15a. After the NO release was finished the sample was kept on the bench at room temperature exposed to air and humidity of over 68 hours. Subsequent exposure to UV light resulted in further release of nitric oxide. The light triggered a slow burst of NO release from 80 to over 500 ppb. The emission immediately stopped when the source of UV light was switched off. The process can be repeated as shown in FIG. 15b.

Example 11—CPO-27 Ni

A sample of 50 mg of CPO-27 Ni prepared following the procedure reported by Morris [23] was activated and NO loaded following the same high pressure technique described above.

Figure 16:
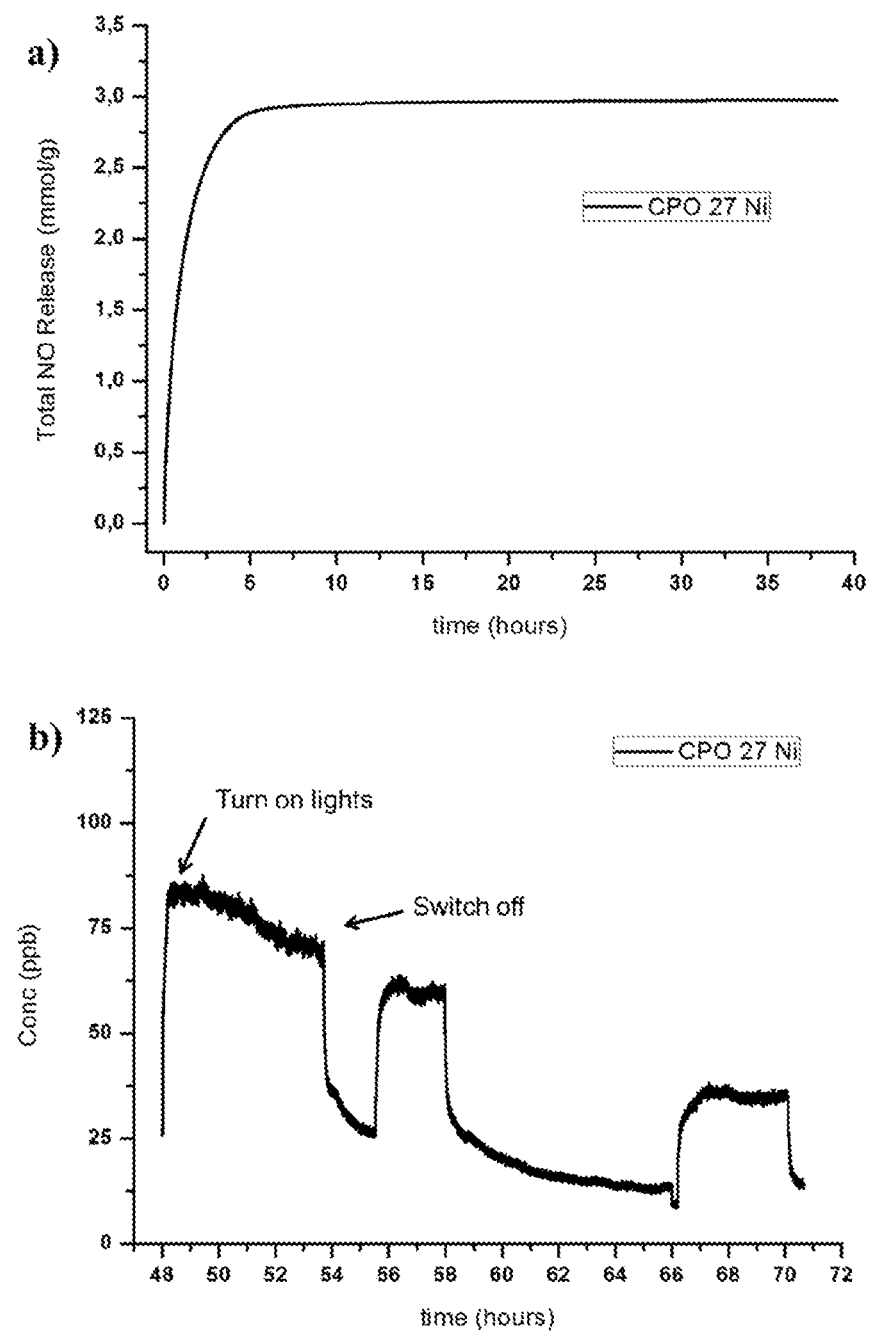
FIG. 16 shows chemiluminescence analysis of total nitric oxide delivery from CPO 27 Ni on contact with humid atmosphere (11% RH) FIG. 16a. NO release from CPO 27 Ni, in contact with humid atmosphere (11% RH), triggered by UV light FIG. 16b. The sample was stored on the bench at room temperature exposed to air and humidity for over 48 hours in between the two analyses.

Total NO release—After exposing the sample to a constant flow of humid nitrogen gas (11% RH) CPO-27 Ni released a total of 2.8 mmol/g of NO over 40 hrs as shown in FIG. 16a. The sample was kept on the bench at room temperature exposed to air and humidity for over 2 days. Further NO release was then triggered by UV light, as shown in FIG. 16b, giving a burst release up to 85 ppb and sustained release over the duration of irradiation. The release of nitric oxide from the framework can be repeatedly triggered by switching the UV light on and off.

Example 12—HKUST-1

A sample of 50 mg of HKUST-1 prepared following the procedure reported by Morris [23] was activated and NO loaded following the same high pressure technique described above.

Figure 17:
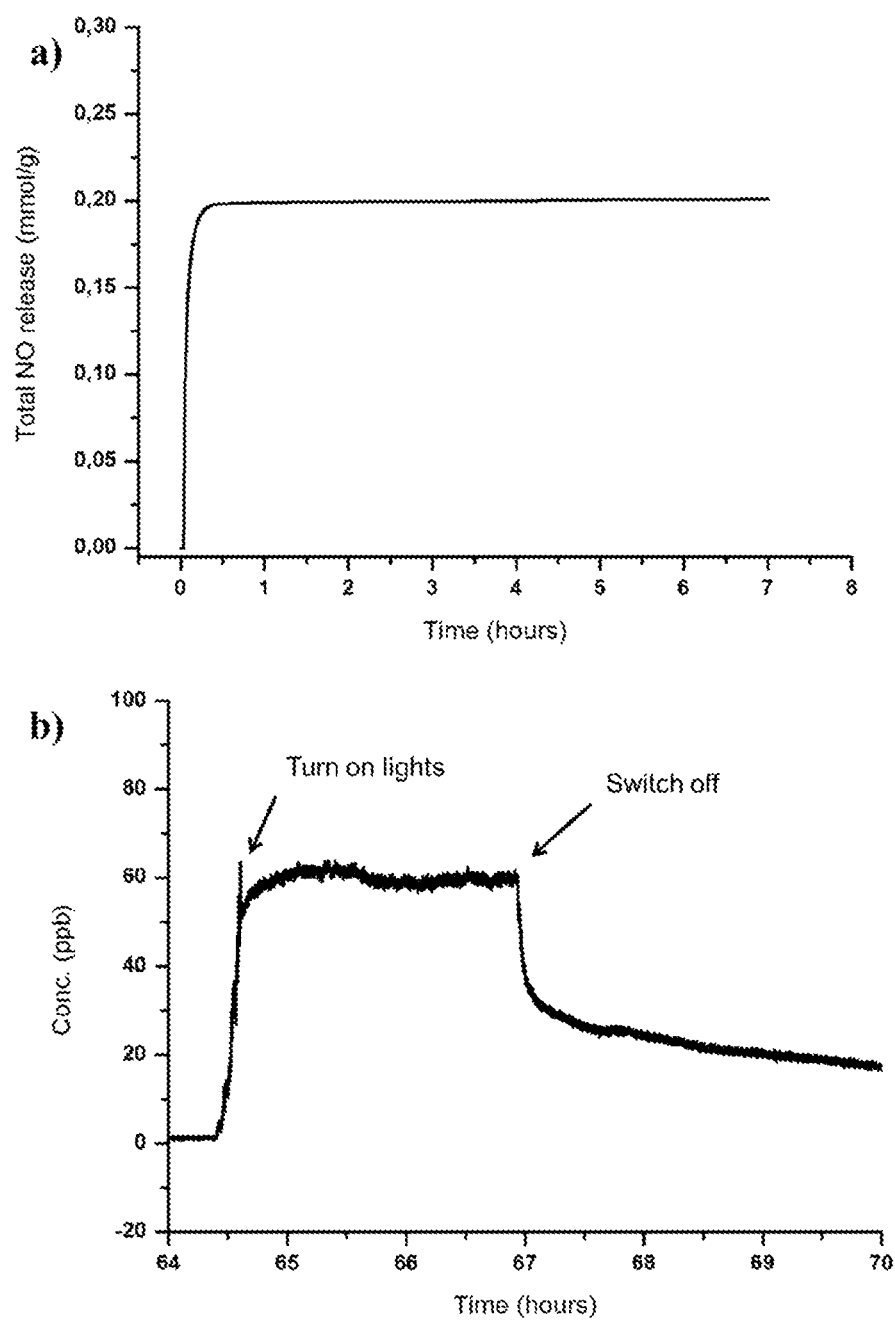
FIG. 17 shows chemiluminescence analysis of total nitric oxide delivery from HKUST-1 on contact with humid atmosphere (11% RH) FIG. 17a. NO release from HKUST-1, in contact with humid atmosphere (11% RH), triggered by UV light FIG. 17b. The sample was stored on the bench at room temperature exposed to air and humidity for over 64 hours in between the two analyses.

Total NO release—An initial release of NO was obtained by exposing the sample to a constant flow of humid nitrogen gas (11% RH). The framework released up to 0.2 mmol/g over 7 hrs as shown in FIG. 17a. After storing the sample on the bench, exposed to humid air for 64 hours, an additional release of NO was triggered using UV light. HKUST-1 released a burst of NO up to 65 ppb with a plateau of 60 ppb for over 1 hr. This trigger mechanism can be repeated and controlled over time (FIG. 17b).

(5) Chlorhexidine-Loaded MOFs

Chlorhexidine and NO-complexed chlorhexidine have been successfully incorporated into and released from MOFs. Moreover, the MOFs have been demonstrated to be capable of releasing NO over time with exposure to UV light and/or a combination of humidity and light.

Chlorhexidine and NO loaded MOFs may be prepared in accordance with the methods of Morris [23] or Lowe [17].

Where the MOF is first loaded with a precursor compound such as a chlorhexidine compound, the exposure of the MOF to nitric oxide may have a double effect; the NO gas is bonded to the MOF and also to the chlorhexidine compound, so as to form a NO and chlorhexidine-NO complex loaded MOF.

NO may be released from the chlorhexidine-NO complex loaded MOF by commonly employed methods including but not limited to exposure to humid air, heat or UV light.

Light triggered release of NO is analogous to that reported above for the NO complexes themselves and for the NO-loaded MOFs. The presence of two different types of NO binding sites may provide for in an increase in the total NO release.

Example 13—Loading of Chlorhexidine into CPO-27 Mg and CPO-27 Ni

Figure 18:
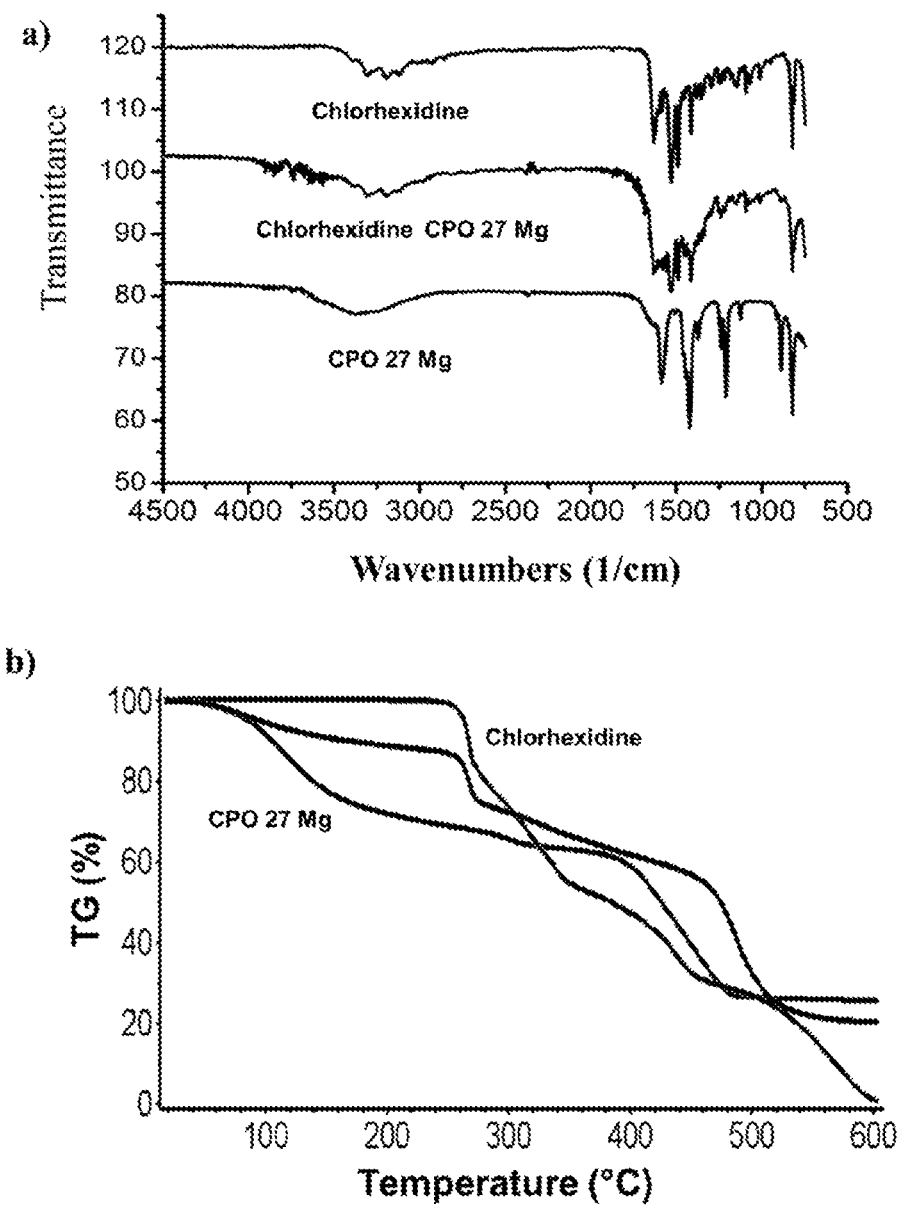
FIG. 18 shows (a) FTIR analysis of chlorhexidine, CPO-27 Mg and chlorhexidine loaded CPO-27 Mg and (b) TGA analysis of chlorhexidine, CPO-27 Mg and chlorhexidine loaded CPO-27 Mg.

A sample of 100 mg of MOF (CPO-27 Mg or CPO-27 Ni) was mixed with 100 mg of chlorhexidine diacetate. The mixture was dehydrated in an oven at 110° C. overnight. The sample vial was then sealed and cooled to room temperature before anhydrous ethanol (100 ml) was introduced through a rubber septum. After 4 days, the suspension was then filtered and washed with ethanol. FT-IR and TGA analysis confirm the presence of chlorhexidine in the framework as shown in FIG. 18.

Figure 19:
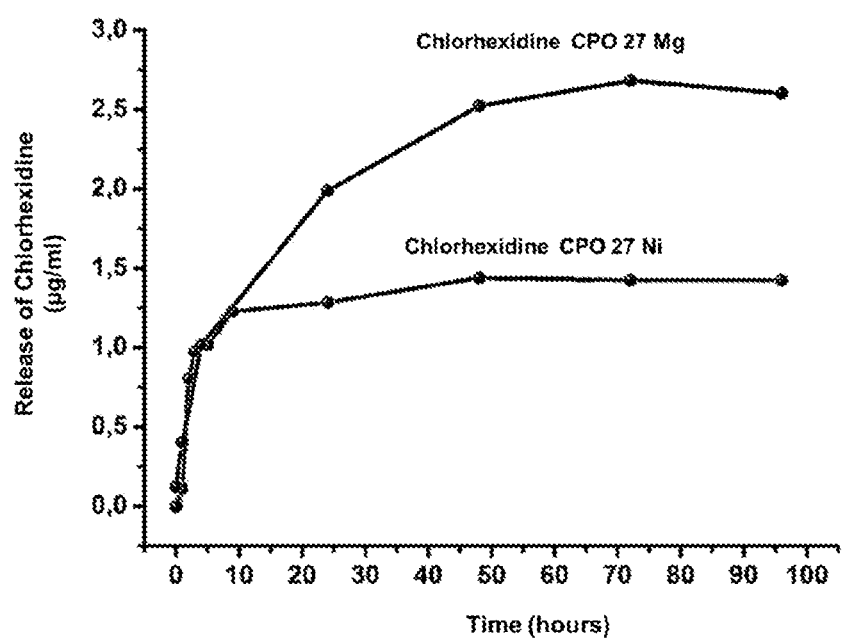
FIG. 19 shows chlorhexidine release from CPO 27 Ni and CPO 27 Mg.

Example 14—Release of Chlorhexidine from CPO-27 Mg and CPO-27 Ni 50 mg of drug-loaded MOF (CPO-27 Mg or CPO-27 Ni) was suspended in 50 ml of methanol. The solution was sampled over time and the concentration of chlorhexidine was detected using UV Vis. FIG. 19 shows the effective release of the drug from the frameworks over time. The drug-loaded CPO-27 Ni shows a burst release reaching 1.3 µg/ml over the first 40 hrs, whereas CPO-27 Mg offers a higher affinity and higher potential release of chlorhexidine over time reaching a plateau of 2.5 µg/ml over 80 hrs.

Example 15—NO Loading and Release from Drug-Loaded CPO-27 Mg

Figure 20:
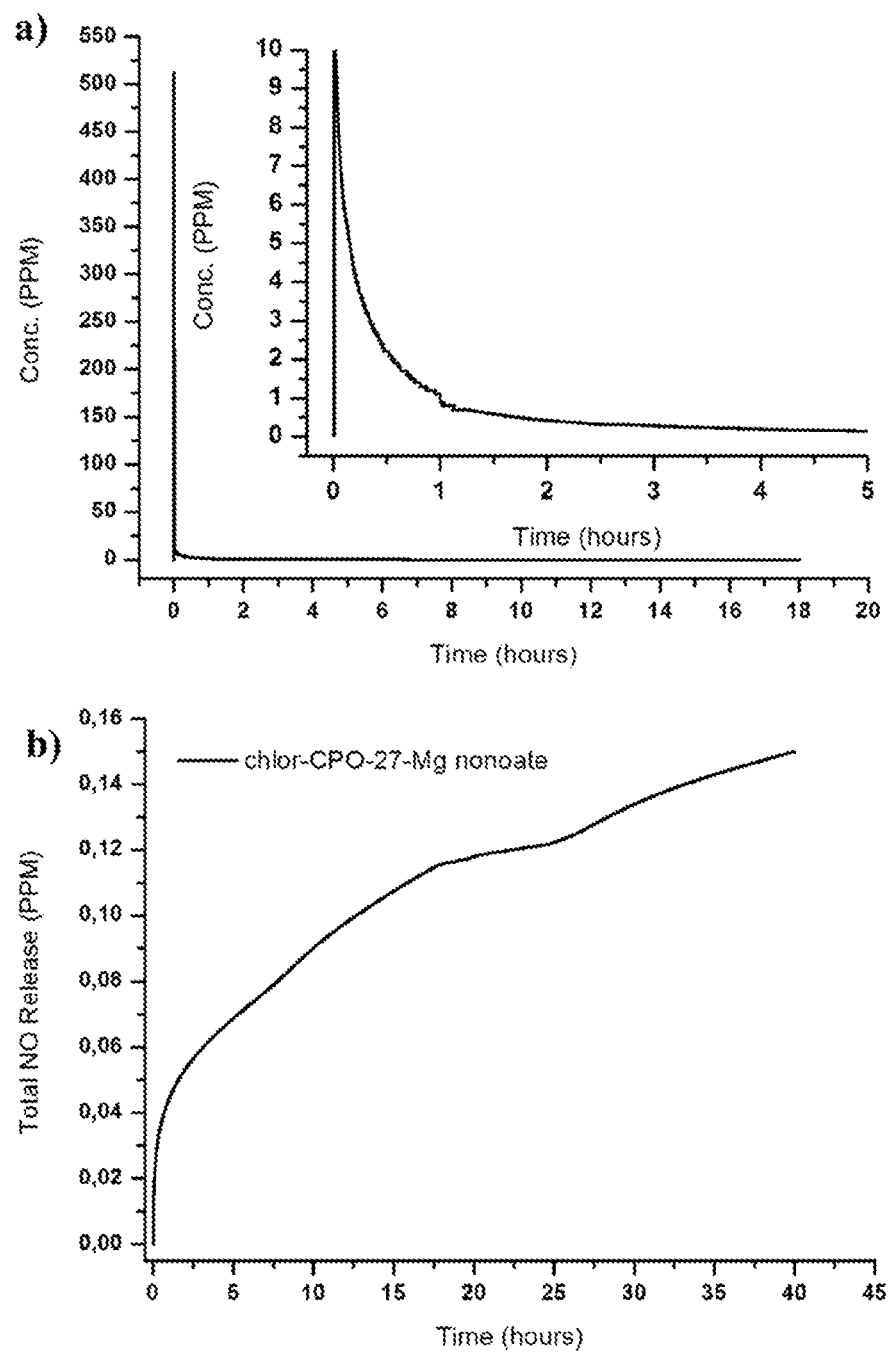
FIG. 20 shows chemiluminescence analysis of total nitric oxide delivery from chlorhexidine loaded CPO 27 Mg on contact with humid atmosphere (11% RH): concentration of NO over time (FIG. 20a) and total NO release over time (FIG. 20b)

A sample of 50 mg of drug-loaded CPO-27 Mg was activated and NO loaded following the high pressure procedure reported above at room temperature. The sample was then exposed to a constant flow of humid nitrogen (11% RH). The quantity of chlorhexidine CPO-27 complex used has a burst release that peaks at 512 PPM. The drug loaded MOF achieves a total NO release of 0.15 mmol/g over 45 hrs as shown in FIG. 20.

Figure 21:
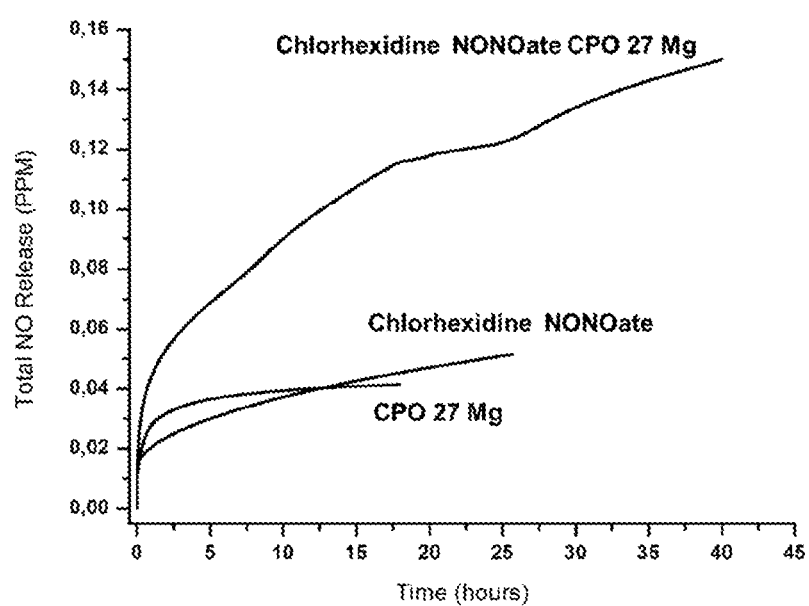
FIG. 21 shows total NO release over time of chlorhexidine acetate, CPO 27 Mg and chlorhexidine-loaded CPO 27 Mg.

Comparison of total NO release from the pure chlorhexidine NO complex, the pure MOF and drug-loaded MOF shows the advantage of the bifunctional material over the two separate moieties, as shown in FIG. 21. The total NO release from NO-complexed chlorhexidine e reaches a maximum of 0.03 mmol/g in 18 hrs and the total NO release from CPO-27 Mg reaches 0.05 mmol/g in 25 hrs. However, the chlorhexidine CPO-27 Mg complex achieves a total NO release of 0.15 mmol/g over 40 hrs due to the combined effect of both moieties.

Figure 22:
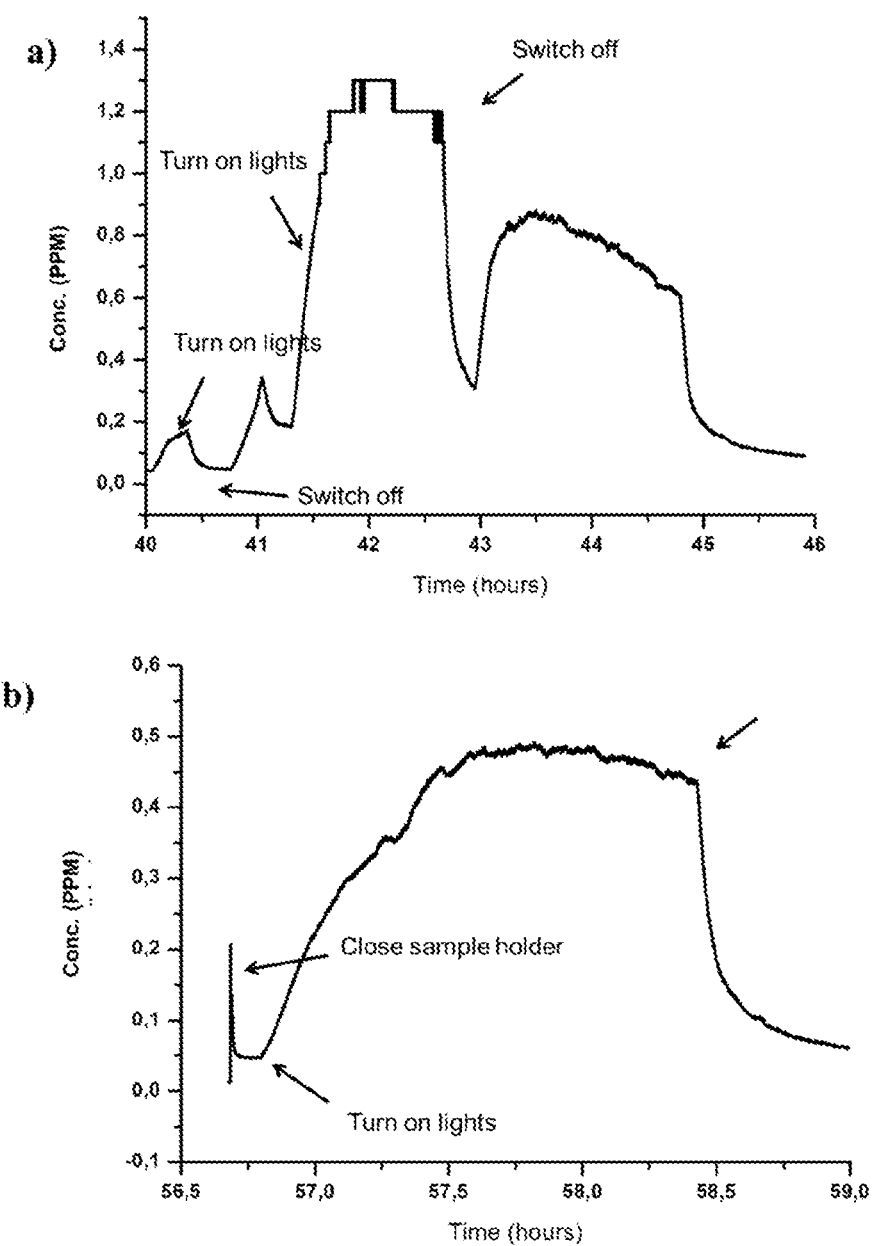
FIG. 22 shows chemiluminescence analysis of nitric oxide delivery from chlorhexidine-loaded CPO 27 Mg, in contact with humid atmosphere (11% RH), triggered by UV light. The sample was stored on the bench at room temperature exposed to air and humidity for over 50 hours in between the two analyses.

The sample of chlorhexidine CPO-27 Mg was kept on the bench at room temperature exposed to air and humidity for over 40 hrs. An additional quantity of NO release was then triggered using UV light, as shown in FIG. 22a. The data shows that the NO dose can be tuned by manipulating the length of exposure to UV-light, over at least 2 hrs (FIG. 22b). The light triggered mechanism repeatedly controls the release of NO gas over time. After initial exposure to UV light, the sample was stored again at room temperature, open to air and humidity for 50 hrs. Further exposure of the sample to UV light triggered an additional release of the gas as shown in FIG. 22b The NO release from the studied quantity of material reached a plateau of 0.5 PPM over 1 hr.

(6) Incorporation of NO Complexed Materials into Matrices for Applications

Each of the above materials, including drug NONOates and/or N-nitroso compounds (chlorhexidine salts and ciprofloxacin), MOFs, and drug loaded MOFs can be incorporated into different matrices. These matrices include but are not restricted to resins and binders (such as those used in paints, inks and coatings for example), creams, ointments, polymers, ceramics and glasses, particularly those employed in healthcare and medical applications (e.g. devices, dressings and topical treatments), or where antiseptic/antimicrobial performance is required (e.g. coatings on surfaces).

The materials can be introduced into these matrices by any appropriate means such as, but not limited to, milling, high speed/sheer mixing, extrusion, electrospinning, casting and moulding. The materials may be employed in a coating on, for example, textiles, plastic, metal, wooden and glass surfaces. This could be achieved by any appropriate means, for example dispersing the material in a resin to be applied by painting, dip coating, spray coating, printing etc. Powder coating can also be employed where appropriate. Additional agents such as dispersion and rheology modifiers may be employed as appropriate and as necessary to aid formulation.

Example 16—Chlorhexidine Release from Polymer Containing Chlorhexidine-Loaded CPO-27 Ni A polyurethane polymer was chosen as a casting material as it is commonly used in catheters. A sample of CPO-27 Ni was drug loaded following the procedure previously reported by Morris et al [23]. The drug loaded MOF was suspended in THF using a high sheer homogeniser and dispersed in predissolved polyurethane. The mixture was solvent cast using doctor blade techniques to produce a ~100 μm thick film.

Figure 23:
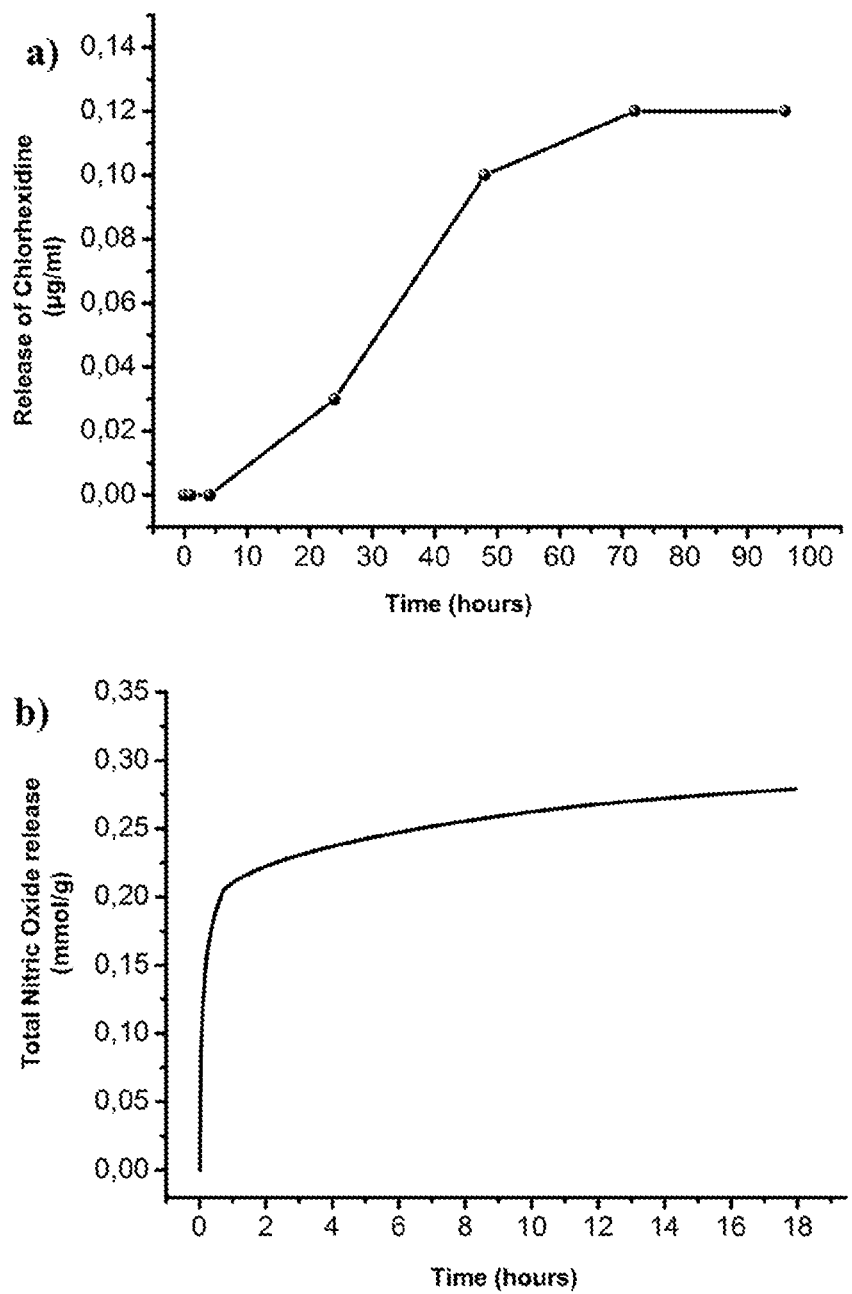
FIG. 23a shows chlorhexidine release from CPO 27 Ni cast in a polyurethane film.
FIG. 23b chemiluminescence analysis of total nitric oxide delivery from chlorhexidine-loaded CPO 27 Ni cast in a polyurethane film, triggered by humid atmosphere (11% RH).

The films were suspended in an appropriated volume of methanol. The solution was sampled over time and the concentration of chlorhexidine was detected using UV spectroscopy. FIG. 23a shows the drug release from the loaded polymer. The release reached a maximum of 0.12 m/ml in 70 hrs.

Example 17—NO Release from Polyurethane Containing Chlorhexidine NO Complexloaded CPO-27 Ni MOF-loaded films (prepared as outlined above) were dehydrated and NO loaded following the previously reported procedure. FIG. 23b shows the total NO release from chlorhexidine loaded CPO-27 Ni cast in a polyurethane polymer when exposed to humid air. The sample delivered a maximum of 0.25 mmol/g after 8 hrs.

REFERENCES

1. S. Pal, E. J. Yoon, Y. K. Tak, E. Choi, and J. M. Song, *J. Am. Chem. Soc.*, 2009, 131 (44), 16147-16155
2. R. E. Morris and P. S. Wheatley, *Angew. Chem. Int. Ed.*, 2008, 47, 4966
3. A. C. McKinlay, B. Xiao, D. S. Wragg, P. S. Wheatley, I. L. Megson and R. E. Morris, *J. Am. Chem. Soc.*, 2008, 130, 10440
4. P. D. C. Dietzel, B. Panella, M. Hirscher, R. Blom and H. Fjellveg, *Chem. Comm.*, 2006, 9, 959
5. P. D. C. Dietzel, R. E. Johnsen, R. Blom and H. Fjellveg, *Chem. Eur. J.* 2008, 14, 2389
6. N. L. Rosi, J. Kim, M. Eddaoudi, B. Chen, M. O'Keeffe and O. M. Yaghi, *J. Am. Chem. Soc*, 2005, 127, 1504
7. P. K. Allan, P. S. Wheatley, D. Aldous, M. I. Mohideen, G. de Weireld, S. Vaesen, R. E. Morris, *Dalton Transactions*, 2012, 41, 14, 4060-4066
8. R. Morris, P. S. Wheatley, WO 2008/020218 A1
9. Z. Bao, S. Alnemrat, L. Yu, I. Vasiliev, Q. Ren, X. Lu and S. Deng, *Langmuir*, 2011, 27, 13554
10. D. J. Tranchemontagne, J. R. Hunt and O. M. Yaghi, *Tetrahedron*, 2008, 64, 8553
11. H. Du, J. Bai, C. Zuo, Z. Xin and J. Hu, *Cryst. Eng. Comm.*, 2011, 13, 3314
12. J.-X. Chen and S.-X. Liu, *Huaxue Xuebao*, 2004, 23, 2323
13. K. E. Holmes, P. F. Kelly and M. R. J. Elsegood, *Dalton Trans.*, 2004, 3488
14. N. E. Ghermani, G. Morgant, J. d'Angelo, D. Desmaele, B. Fraisse, F. Bonhomme, E. Dichi and M. Sgahier, *Polyhedron*, 2007, 26, 2880
15. E. J. Martinez, J. J. Talley, K. D. Jerome, T. L. Boehm. WO2014012074 A3
16. A. El-Emam, E. Glusa, J. Lehmann, *Eur. J. Med. Chem.*, 2008, 51, 713-716
17. A. Lowe, P. Chittajallua, Q. Gongb, J. Lib, K. J. Balkus Jr., *Micropor. Mesopor. Mat.*, 2013, 181, 17-22
18. S. Diring, K. Kamei and S. Furukawa, *Nature Communications* 2013, 2684 (4)
19. B. J. Heilman, S.t R. J. Oliver, and P. K. Mascharak, *J. Am. Chem. Soc.*, 2012, 134 (28), 11573-11582
20. E. J. Martinez, J. J. Talley, K. D. Jerome, T. L. Boehm, WO2014012074 A3
21. J. G. Nguyen, K. K. Tanabe and S. M. Cohen, *Cryst. Eng. Comm*, 2010, 12, 2335-2338
22. S. Rojas, P. S. Wheatley, R. E. Morris and E. Barea, *Cryst. Eng. Comm,* 2013, 15, 9364-9367
23. R. E. Morris, P. S. Wheatley, S. Warrender, M. Duncan, WO 2013186542 A1
24. S. Pal, E. J. Yoon, S. H. Park, E. C. Choi and J. M. Song, *J. Antimicrob. Chemother.*, 2010; 65(10), 2134-40.
25. L. K. Keefer, J. L. Flippen-Anderson, C. George, A. P. Shanklin, T. M. Dunams, E. S. Sagan and D. S. Bohle, *J. Am. Chem. Soc.* 2001, 13; 123(23):5465-72

The invention claimed is:

1. A biguanide containing compound comprising one or more NO molecules bound thereto, wherein the biguanide is obtained by reacting a precursor compound having the general structure I:

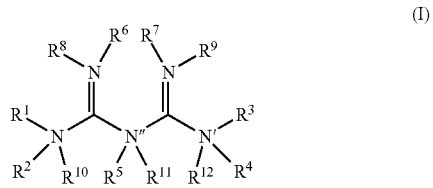

with NO gas or a nitrosylating agent in order to generate a biguanide containing compound comprising one or more NO molecules bound thereto; wherein $R_1$-$R_5$ independently comprise (a) substituted or unsubstituted $C_1$-$C_{10}$ alkyl-, (b) substituted or unsubstituted aryl-, (c) H, with the proviso that $R_2$ is not H when $R_1$ is H, and $R_4$ is not H when $R_3$ is H or (d) a bond or linking group to a further structure (I) as defined above, or to a polymer or other macromolecule;

$R_6$ and $R_7$ independently are H, $C_1$-$C_{10}$ alkyl- or aryl- or together or independently represent a coordinated metal ion;

$R_8$-$R_{12}$ are each optional, but when present result in the N atom to which they are bound becoming positively charged and independently comprise H, $C_1$-$C_{10}$ alkyl- or aryl-; and substituents independently comprise $C_1$-$C_{10}$ alkyl-, phenyl- or halogen.

2. The biguanide containing compound of claim 1, wherein the coordinated metal ion is selected from the group consisting of silver, copper, nickel, zinc, magnesium and calcium.

3. The biguanide containing compound of claim 1 wherein $R_5$-$R_7$ and $R_8$-$R_{12}$, when present, are H.

4. The biguanide containing compound of claim 1, which is N,N'-bi-substituted, N,N,N'-tri-substituted, N,N',N'-tri-substituted or N,N,N',N'-tetra-substituted molecule wherein each substituent is a non-H substituent.

5. A porous framework material comprising an extra-framework NO complexed biguanide containing compound of claim 1 within the internal pores and/or channels of the porous framework material.

6. The porous framework material of claim 5 which is a metal organic framework material (MOF).

7. A porous framework material according to claim 5 that releases NO from the extra-framework biguanide containing compound and/or the released biguanide compound, wherein the rate of release of NO optionally is altered by an external stimulus.

8. The porous framework material of claim 5 wherein the external stimulus is a change in temperature or pressure, irradiation with light, or contact with another species.

9. A method of preparing a porous framework material of claim 5;
the method comprising:
- forming a NO complexed compound from a suitable precursor compound; and
- contacting a porous framework material with the NO complexed compound so as to adsorb the NO complexed compound into the pores and/or channels of the porous framework material;

or the method comprising:
- forming a porous framework material which comprises a precursor compound capable of reacting to form a NO complexed compound in the pores and/or channels of the porous framework material; and
- forming an extra-framework NO complexed compound in situ by contacting the porous framework material with NO.

10. A method of releasing NO, comprising providing a porous framework material of claim 5 having an extra-framework NO complexed compound within the internal pores and/or channels of the porous framework material, contacting said porous framework material with a medium into which the NO is to be released, and releasing NO into the medium, and optionally further comprising applying an external stimulus to the porous framework material, wherein the external stimulus comprises an increase in temperature, a change in pH, irradiation with light, a change in pressure, or a combination thereof and/or wherein the external stimulus comprises contacting the porous framework material with another species.

11. The method of claim 10 wherein the another species is water.

12. A pharmaceutical, neutraceutical or cosmetic preparation comprising a porous framework material of claim 5, together with a pharmaceutical, neutraceutical or cosmetic carrier therefor.

* * * * *